US012037653B2

(12) United States Patent
Inchingolo et al.

(10) Patent No.: US 12,037,653 B2
(45) Date of Patent: Jul. 16, 2024

(54) MULTIPLEX RT-PCR METHOD AND KIT FOR THE DETECTION OF MULTIPLE VIRUSES OF THE CORONAVIRIDAE FAMILY: SARS-CoV2, SARS-CoV, HCoV, AND MERS-CoV

(71) Applicants: UNIVERSITA' DEGLI STUDI ALDO MORO, Bari (IT); UNIVERSITY PHAN CHAU TRINH, Quang Nam Province (VN)

(72) Inventors: Francesco Inchingolo, Bari (IT); Andrea Ballini, Bari (IT); Ciro Gargiulo Isacco, Bari (IT); Gianna Dipalma, Bari (IT); Alessio Danilo Inchingolo, Bari (IT); Angelo Michele Inchingolo, Bari (IT); Cao Diem Kieu Nguyen, Bari (IT); Van Hung Pham, Ho Chi Minh (VN)

(73) Assignees: UNIVERSITÀ DEGLI STUDI ALDO MORO, Bari (IT); UNIVERSITY PHAN CHAU TRINH, Quang Nam Province (VN)

( * ) Notice: Subject to any disclaimer, the term of this patent is extended or adjusted under 35 U.S.C. 154(b) by 597 days.

(21) Appl. No.: 17/034,407

(22) Filed: Sep. 28, 2020

(65) Prior Publication Data
US 2021/0363602 A1 Nov. 25, 2021

(30) Foreign Application Priority Data
May 20, 2020 (IT) .................. 102020000011701

(51) Int. Cl.
C12Q 1/70 (2006.01)
(52) U.S. Cl.
CPC ..... *C12Q 1/701* (2013.01); *C12N 2770/20011* (2013.01); *C12Q 2537/143* (2013.01); *C12Q 2600/16* (2013.01)
(58) Field of Classification Search
CPC .............. C12Q 1/701; C12Q 2537/143; C12Q 2600/16; C12N 2770/20011
See application file for complete search history.

(56) References Cited

U.S. PATENT DOCUMENTS 8,057,993 B2 * 11/2011 Ecker ..................... C12Q 1/701
435/6.12

FOREIGN PATENT DOCUMENTS

| CN | 110157839 A | 8/2019 |
| CN | 111139317 A | 5/2020 |
| KR | 101916899 B1 | 11/2018 |

OTHER PUBLICATIONS

Corman, V. M., et al., Jan. 2020, Detection of 2019 novel coronavirus (2019-nCoV) by real-time RT-PCR, Euro Surveill 25(3): pii=2000045, pp. 1-8, published Jan. 23, 2020.*
Department of Health & Human Services, Jan. 24, 2020, 2019-Novel Coronavirus (2019-nCoV) Real-time rRT-PCR Panel Primers and Probes, Division of Viral Diseases, Public Health Service, Centers for Disease Control and Prevention (CDC), Atlanta, GA.*
Lu, X., et al., Jan. 2014, Real-Time Reverse Transcription-PCR Assay Panel for Middle East Respiratory Syndrome Coronavirus, J. Clin. Microbiol. 52(1):67-75.*
Rockett, R., 2010, Chapter 42: Human Coronaviruses, in PCR for Clinical Microbiology, Schuller, M., et al., eds., Springer Science, pp. 273-275.*
Yu, X., et al., 2015, Development of a real-time reverse transcription loop-mediated isothermal amplification method for the rapid detection of porcine epidemic diarrhea virus, Virol. J. 12(76):1-8.*
Ishige, Takayuki et al., "Highly sensitive detection of SARS-CoV-2 RNA by multiplex rRT-PCR for molecular diagnosis of COVID-19 by clinical laboratories", Clinica Chimica Acta, vol. 507, 2020, pp. 139-142.
Who Team, "Molecular assays to diagnose COVID-19: Summary table of available protocols", (Jan. 24, 2020), URL: https://www.who.int/docs/default-source/coronaviruse/whoinhouseassays.pdf?sfvrsn=de3a76aa_2&download=true, (2020), XP055732018 [Y] 7,9-13 * p. 7 *.
Corman et al., "Detection of 2019 novel coronavirus (2019-nCoV) by real-time RT-PCR", Eurosurveillance.org, Jan. 23, 2020, vol. 25, No. 3, pp. 23-30.
Rockett, Rebecca, "Chapter 42: Human Coronaviruses : An Australian and International Perspective", PCR for Clinical Microbiology : An Australian and International Perspective, 2010, pp. 273-275.
Corman et al., "Detection of a novel human coronavirus by real-time reverse-transcription polymerase chain reaction", Rapid Communications, Eurosurveillance, Fr, Sep. 27, 2012, vol. 17, No. 39, 1-7.
Yu, Xuewu et al., "Development of a real-time reverse transcription loop-mediated isothermal amplification method for the rapid detection of porcine epidemic diarrhea virus", Virology Journal, May 14, 2015, vol. 12:76, pp. 1-8.

(Continued)

Primary Examiner — Jeffrey S Parkin
(74) Attorney, Agent, or Firm — Rothwell, Figg, Ernst and Manbeck, P.C.

(57) ABSTRACT

The invention relates to a diagnostic kit for multiple detection of 4 viruses of the Family Coronaviridae: HCoV, SARS-CoV, MERS-CoV and the SARS-CoV-2 viral strain that has caused a pandemic of the disease known as COVID-19. The kit uses a "One-Step" approach with quantitative gene amplification after backward transcription of the viral genome (rRT-PCR).

In order to avoid potential false negatives, the invention contains a double control using Porcine Epidemic Diarrhoea Virus (PEDV-CoV) and Ribonuclease P (RNase P-RP).

8 Claims, 19 Drawing Sheets
Specification includes a Sequence Listing.

(56) References Cited

OTHER PUBLICATIONS

Extended European Search Report in EP20197796.4 dated Mar. 11, 2021 (11 pages).
Anonymous, "Qiagen RNeasy Micro Handbook", Qiagen, (Apr. 2003), pp. 1-76, URL: https://www.qiagen.com/, (May 27, 2020), XP055698767 [I] 8 * pp. 4,22,33.

* cited by examiner

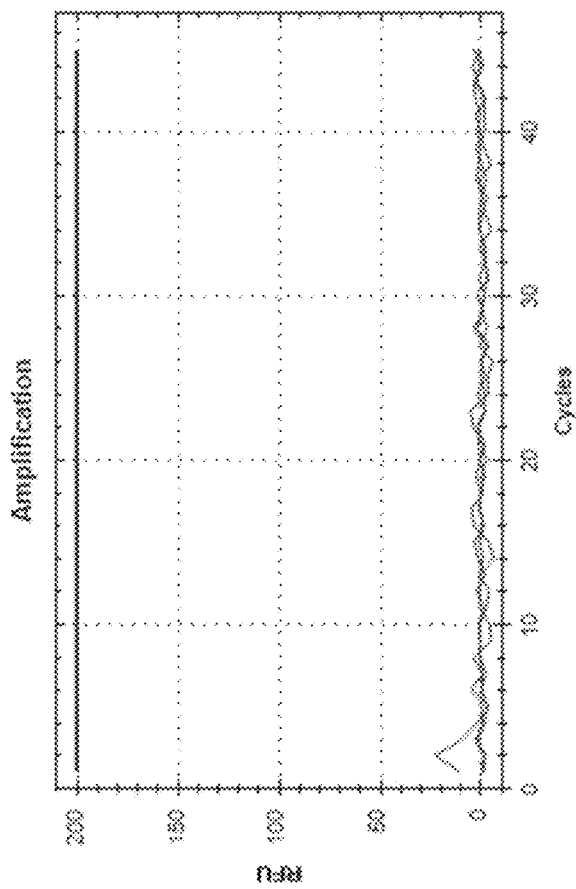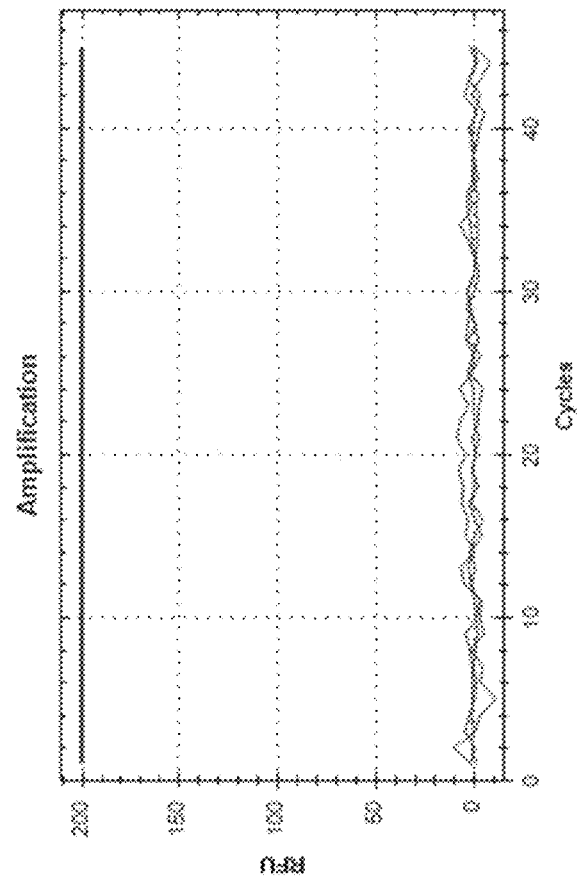
Figure 10A
Figure 10B

MULTIPLEX RT-PCR METHOD AND KIT FOR THE DETECTION OF MULTIPLE VIRUSES OF THE CORONAVIRIDAE FAMILY: SARS-CoV2, SARS-CoV, HCoV, AND MERS-CoV

CROSS-REFERENCE TO RELATED APPLICATION

This application claims the benefit of Italian Patent Application No. 102020000011701 filed on May 20, 2020, the disclosure of which is incorporated herein in its entirety by reference.

The present application includes a Sequence Listing filed in electronic format. The Sequence Listing is entitled "4863-102_ST25.txt" created on Nov. 2, 2020 and is 5,000 bytes in size. The information in the electronic format of the Sequence Listing is part of the present application and is incorporated herein by reference in its entirety.

BACKGROUND

In a general aspect, the present invention relates to methods and diagnostic devices intended for the detection of viruses of the family Coronaviridae.

As it is unfortunately known from recent events connected with the current pandemic called Covid-19, the management of health-related emergencies on a large scale poses some weaknesses that require a fast response from the public and private health services involved.

In fact, in case of epidemics or pandemics like those caused by viruses of the family Coronaviridae (also referred to as Coronaviruses), such as SARS-CoV-2, SARS-CoV, MERS-CoV, HCoV, it is important to be able to quickly establish the health conditions of potentially affected subjects, not only to save human lives, but also know the spread of the infection and take all necessary sanitary actions.

As in the past, diagnostic technologies have been specifically developed for this purpose, and there is awareness that the existing tools should be improved through instrumental and/or diagnostic tests which may give a first indication that, being typically obtained along with a clinical evaluation of the symptoms, will provide a diagnosis of a patient's health conditions in a relatively short time, in a safe manner, and with high sensitivity and specificity.

However, the emerging of recent or old mutated harmful pathogens always causes a global threat.

The last two decades have seen the menace of particularly dangerous mutated flu-virus strains; six were detected, four of which are known to cause mild respiratory symptoms in immune-competent individuals, i.e. Human Coronavirus HCoV-229E, HCoV-NL63, HCoV-OC43, HCoV-HKU1, whereas the other two, i.e. Middle East Respiratory Syndrome coronavirus (MERS-CoV) and Severe Acute Respiratory Syndrome coronavirus (SARS-CoV) caused worldwide epidemics with a high mortality rate.

All members of the Coronavirus family are characterized by a unique biochemical structure composed of Porcine Epidemic Diarrhoea Virus (PEDV) with a single strand of ribonucleic acid (RNA). Novel mutated strains represent a severe risk due to the wide distribution of coronavirus' genetic diversity, with frequent genomic recombination. These include human coronavirus HCoV-229E, which, after having been originated from a bat Alphacoronavirus, passed again into an animal host, generating the porcine epidemic diarrhoea virus (PEDV), or the even more important human coronavirus SARS-CoV, which appears to have its reservoir in bats. This propensity for quickly adapting themselves to new hosts or tissues or ecologic niches is due to the high genomic diversity that characterizes coronaviruses and permits the origination of new species. In particular, bats are the natural reservoir of numerous Alpha- and Beta coronaviruses, among which there are viruses strictly correlated genetically with the aetiologic agent of the severe acute respiratory syndrome (SARS), which emerged in 2002 in the Guangdong province in China and then spread worldwide with epidemic characteristics. These bat coronaviruses correlated with the SARS virus, i.e. SARS-like coronavirus (SARS-like CoV), have been detected in Asia, Africa and Europe. Several theories have been proposed to explain their origin, according to one of which they first appeared in African bats and then spread in Europe and Asia.

Between November and December 2019, a new type of coronavirus named Severe Acute Respiratory Syndrome Coronavirus 2 (SARS-CoV-2), which is the causing agent of Coronavirus Disease 2019, otherwise known as COVID-19, and initially referred to as 2019-nCoV, has rapidly begun spreading uncontrollably in the Wuhan province in China and then in the rest of the world, causing a global pandemic. The virus extracted from lower respiratory tract samples of several infected patients confirmed the genetic marks of the coronavirus. The typical symptoms may be severe pneumonia, including fever, physical weakness and fatigue, dry cough, and respiratory distress.

The aggressive nature of SARS-CoV-2 is particularly evident in individuals with pre-existent comorbidities. Evidence has shown that SARS-CoV-2 uses angiotensin converting enzyme 2 (ACE2) as a preferred receptor to get in and start infecting. The ACE2 messenger RNA is highly expressed and stabilized by a neutral amino acid transporter (B0AT1) in the gastrointestinal system, providing a prerequisite for SARS-CoV-2 infection.

The rise in the number of infected patients and deaths is of great concern especially because symptoms are vague and similar to those of other forms of flu infection.

According to the latest guidelines published by the World Health Organization (WHO), the diagnosis of COVID-19 must be confirmed by quantitative reverse transcription polymerase chain reaction (hereafter briefly referred to as rRT-PCR) or gene sequencing of specimens obtained from oropharyngeal, sputum or blood molecular samples.

However, limitations due to logistics, as well as the low sensitivity and specificity of the diagnostic tools currently available, have been reported as the main causes for the high incidence of false negative or positive results.

At present, for the COVID-19 pandemic, the diagnostic testing procedure is similar to the one that was applied almost two decades ago for SARS-CoV, which envisaged the collection of specimens, preferably from the respiratory system, e.g. nasopharyngeal aspirates, or plasma or serum, to be analysed. On last March 22, the World Health Organization (WHO) published the interim guidance "Laboratory testing strategy recommendations for COVID-19", wherein the most preferred test is rRT-PCR, which can confirm the presence of viral RNA in clinical samples, assessing both the activity of the virus and progression of the disease.

However, SARS-CoV-2 is still evolving and, as it was for the previous SARS-CoV coronavirus pandemic infection, the currently available tests have shown some limitations.

The main concerns are mostly related to false negative/positive outcomes, risks caused by the low sensitivity of the screening procedures, incongruous specimen collection measures, long sampling times, and processing errors.

Furthermore, following the WHO recommendations envisaging the application of a procedure similar to the one that was adopted during the SARS-CoV pandemic almost two decades ago, sequential samples from suspected patients should be kept for future use.

This implies, therefore, that health authorities should collect and store clinical and contact history data in order to generate a clear logarithm that will show the virus-specific traits and patterns and its way of transmission.

Patients' samples should be available for rRT-PCR analysis, virus culture, antigen detection, and serological antibody testing. The WHO is warmly supporting local Governments in creating a capillary network of designate health task forces which include centres for prevention and treatment and laboratories for investigation and/or referral of specimens from possible COVID-19 patients.

Therefore, because of the existing situation and unpredictable manifestations of the novel infection, it is stated that the main object of the present invention is propose a new analytical method for a rapid and effective diagnosis of COVID-19 (SARS-CoV-2) as well as MERS-CoV, SARS-CoV and HCoV.

SUMMARY OF THE INVENTION

The invention is based on the use of the rRT-PCR test for quantitative detection of nucleic acid of a plurality of viruses representative of some diseases connected with the Family Coronaviridae, such as SARS-CoV-2, SARS-CoV, MERS-CoV and HCoV in respiratory specimens from the upper and lower tracts (e.g. nasopharyngeal or oropharyngeal swabs, sputum, lower respiratory tract aspirate, bronchoalveolar lavage, and nasopharyngeal lavage/aspirate or nasal aspirate), collected from individuals suspected of COVID-19 by their healthcare provider.

The RNA of the SARS-CoV-2 virus is generally detectable in respiratory specimens during the acute phase of infection. According to the laboratory data of the present invention, either positive or negative results are suggestive of SARS-CoV-2 infection; clinical correlation with symptoms and clinical information can confirm the patient's infection condition.

In case of positive results, according to the invention the procedure does not rule out bacterial infection; however, co-infection with other viruses belonging to the Coronavirus family can be assessed, and the identified pathogen can be defined as the cause of the disease.

The present invention requires a negative control (without template) through multiplex (MPL) rRT-PCR, which should be preferably used on every test sample, in order to eliminate any risk of contamination of the sample when the test is carried out.

This control should not be amplified, since it is of molecular grade and nuclease-free; preferably, the control occurs in two stages MPL1, MPL2 by rRT-PCR.

The kit proposed herein detects and amplifies viral nucleic acid isolated by using a standard extraction and purification kit. After purification, the nucleic acid is ready to be amplified in the Real-Time PCR reaction. Each target RNA is then detected thanks to a specific green, yellow, orange or red fluorophore (or fluorochrome); fluorescence signals are measured by the Real-Time PCR instrument, which then provides the final result. The channels that need to be set up on the Plate Editor of the Real-Time PCR instrument are green (FAM), yellow (HEX), orange (TexasRED (R) and red (Cy5).

During the first phase MPL1, all target genes N1, N2, N3 of SARS-CoV-2 must be amplified with the amplification signal in the FAM (N1), TexasRED (N2) and HEX (N3) channels. Amplification of Ribonuclease P (RNase P-RP) (CY5) that belongs to the host epithelial cells may occur depending on the amount of SARS-CoV-2 revealed in the tested sample.

During the second phase MPL2, the E gene (FAM) of SARS-CoV and SARS-CoV-2 and the N gene (HEX) of PEDV must be amplified. Thus, positive templates are needed (COVID-19 N 1-2-3) as the control verifies that the test is performing as intended and is used on every assay plate starting from the addition of Master Mix at a concentration of 10 copies/uL.

BRIEF DESCRIPTION OF DRAWINGS

The features of the invention are specifically set out in the claims attached to this description.

Such features will become more apparent in the following explanations concerning an illustrative, but non-limiting, example of embodiment of the invention, wherein reference will be made to a number of drawings:

FIGS. 10A and 10B show diagrams wherein the negative control shows no amplification signal in MPL1 (10A) and MPL2 (10B).

DETAILED DESCRIPTION

Figure 1:
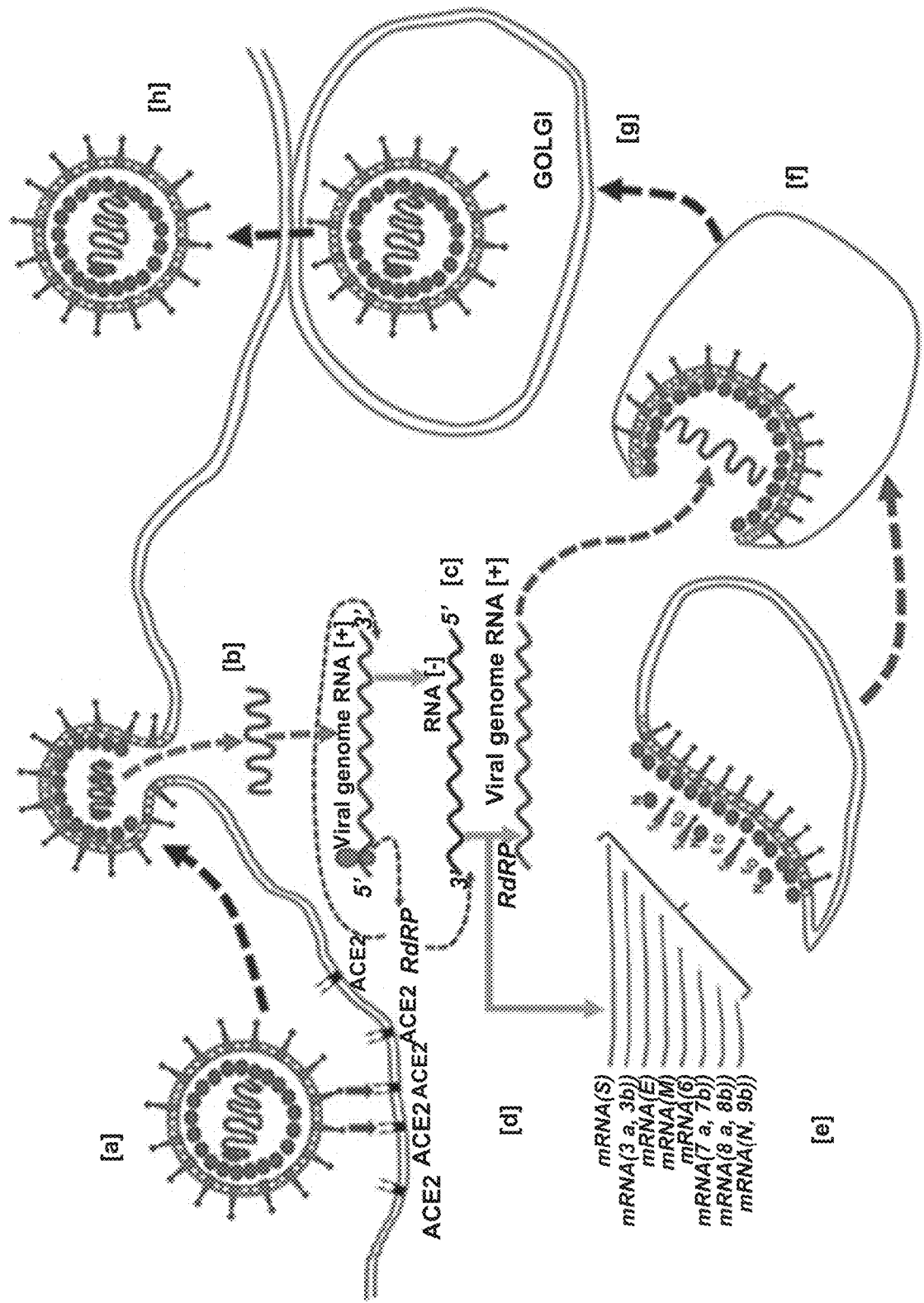
FIG. 1 schematically shows the replication of SARS-CoV-2. The SARS-CoV-2 infectious pathway depends upon the virus RNA. The virus binds to target with its spike proteins on its surface and use it as anchorage. The Spike protein targets the ACE2 cell receptor and enters into the cells by using a special enzyme(TMPRSS2). Once the virion is quietly accommodated, it releases its RNA. From host cell DNA machinery, it is then used to produce virion proteins that are used to replicate more infectious RNA. Proteins and RNA are used in the Golgi apparatus to produce more virus and to be released out: (a) The virus binds to target with its spike proteins on its surface and uses them as anchorage. The Spike protein targets the ACE2 cell receptor and enters into the cells by using a special enzyme (TMPRSS2); (b) After entering the cell, the viral genome will translate the RNA dependent RNA polymerase (RdRP); (c) RdRP will synthesize RNA [−]; (d) RNA [−] is the template for RdPR to synthesize the viral RNA RNA [+] and other mRNAs of the virus; (e) The mRNA will be translated into the structural protein (S, N, E) and the other non-structural proteins of the virus that will accumulate on the reticulo-endothelial membrane of the cells; (f) The reticulo-endothelial membrane will package the viral genome RNA [+] to form the complete virions; (g) The virion will be transferred to Golgi apparatus; (h) the virus will be released out to enter new cells.
Figure 2:
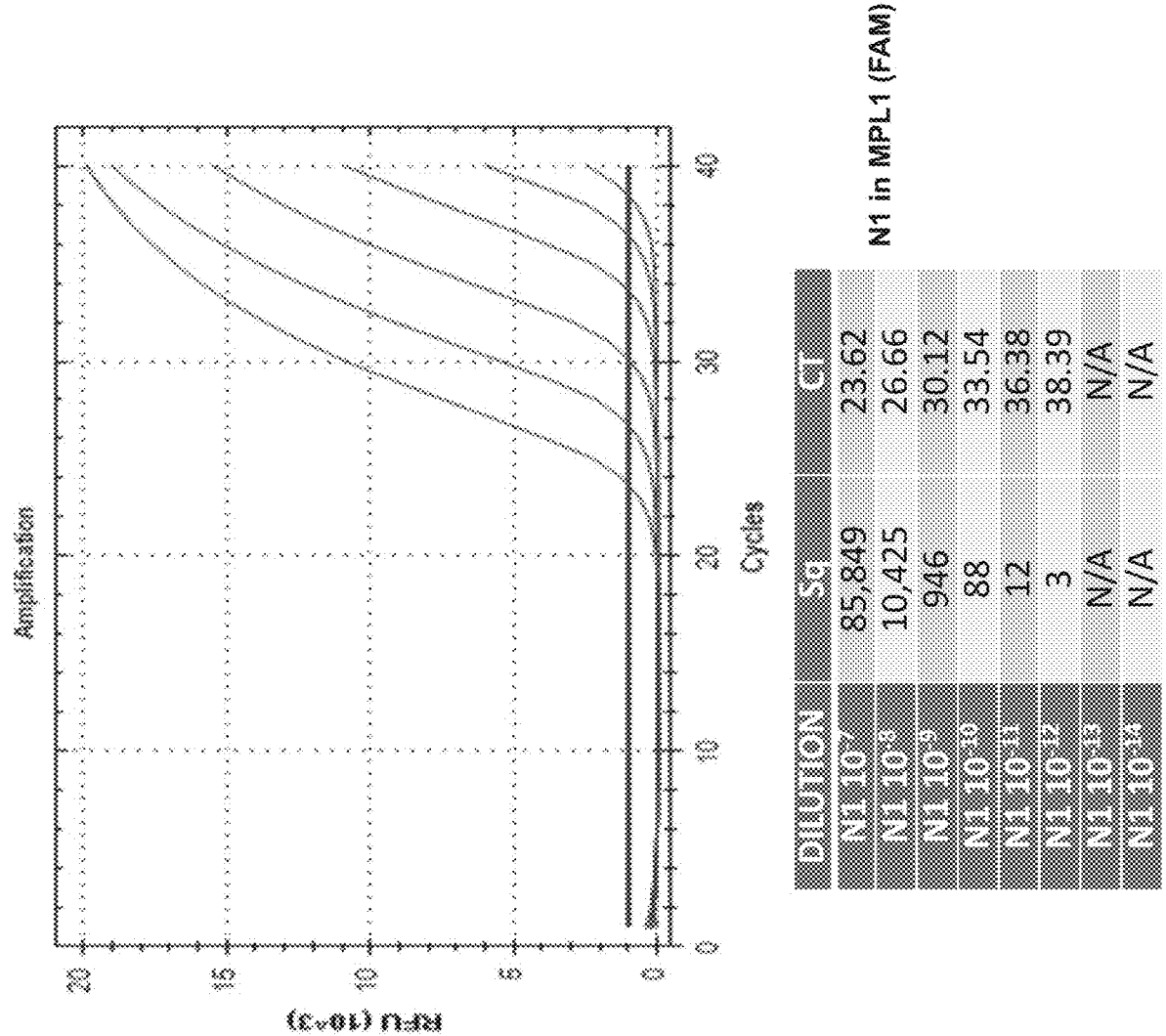
FIG. 2 shows a diagram illustrating the sensitivity of the rRT-PCR step for the detection of the N1 gene of SARS-CoV-2, in accordance with the invention.
Figure 3:
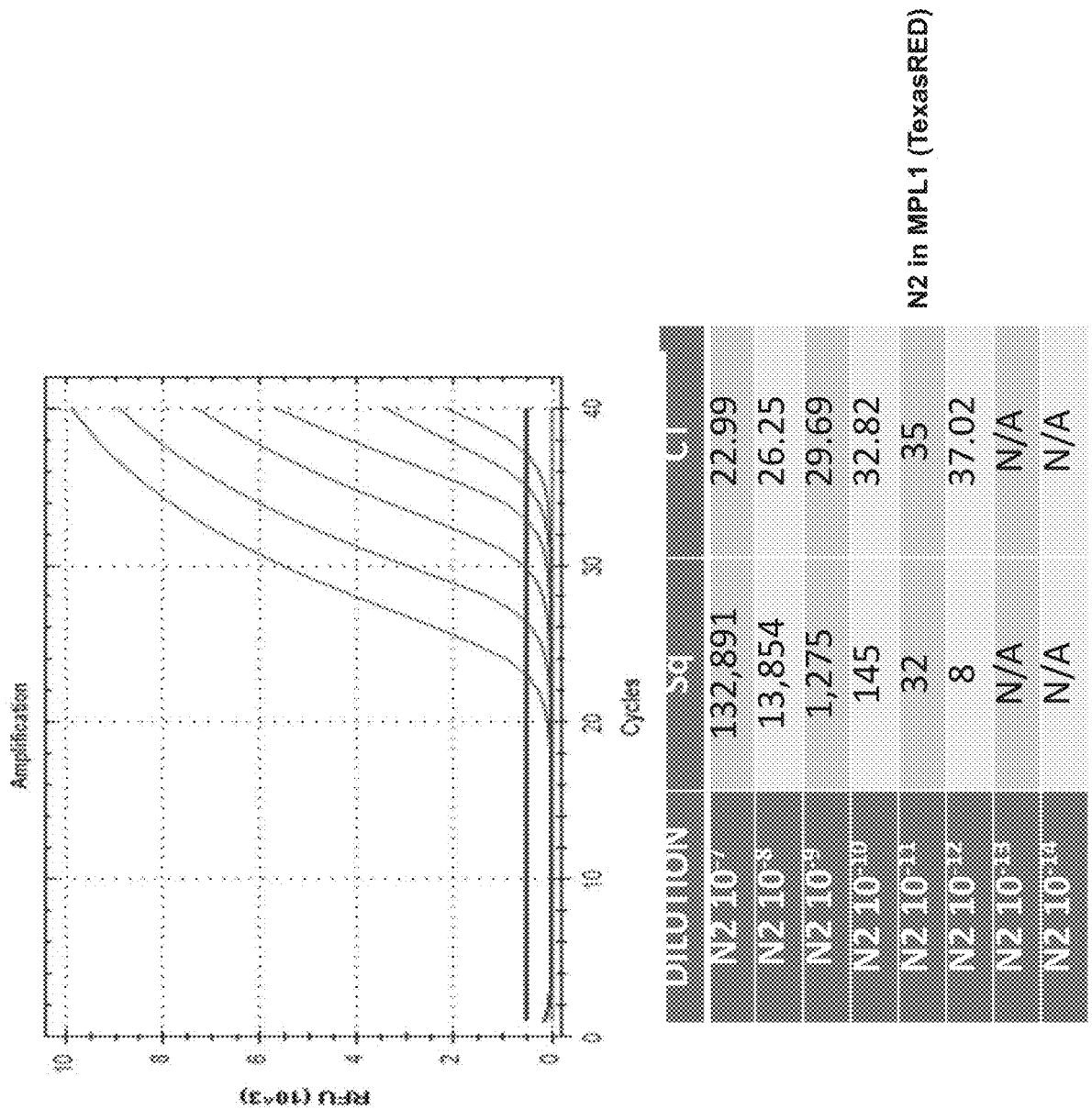
FIG. 3 shows a diagram illustrating the sensitivity of the rRT-PCR step for the detection of the N2 gene of SARS-CoV-2, in accordance with the invention.
Figure 4:
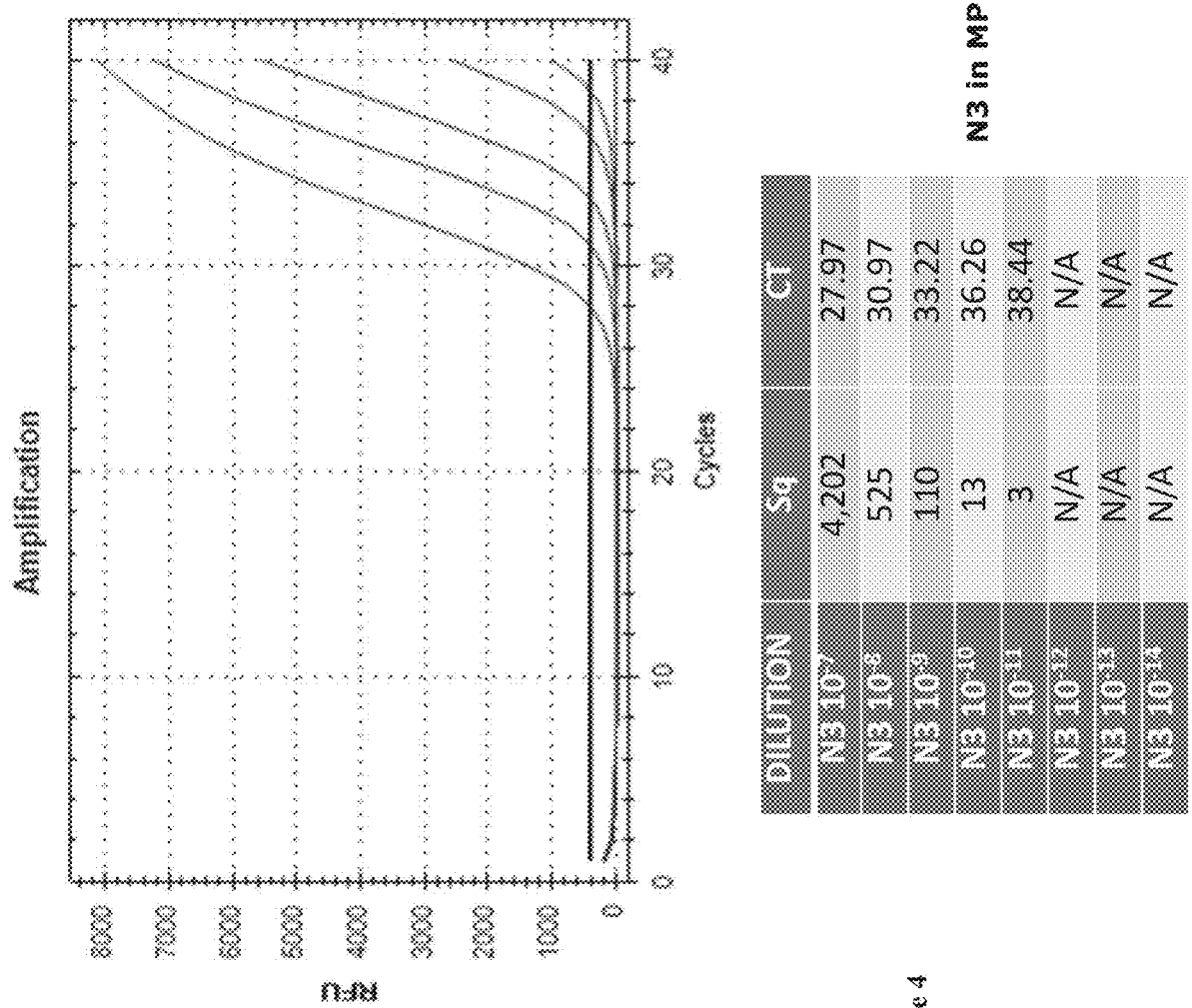
FIG. 4 shows a diagram illustrating the sensitivity of the rRT-PCR step for the detection of the N3 gene of SARS-CoV-2, in accordance with the invention.
Figure 5:
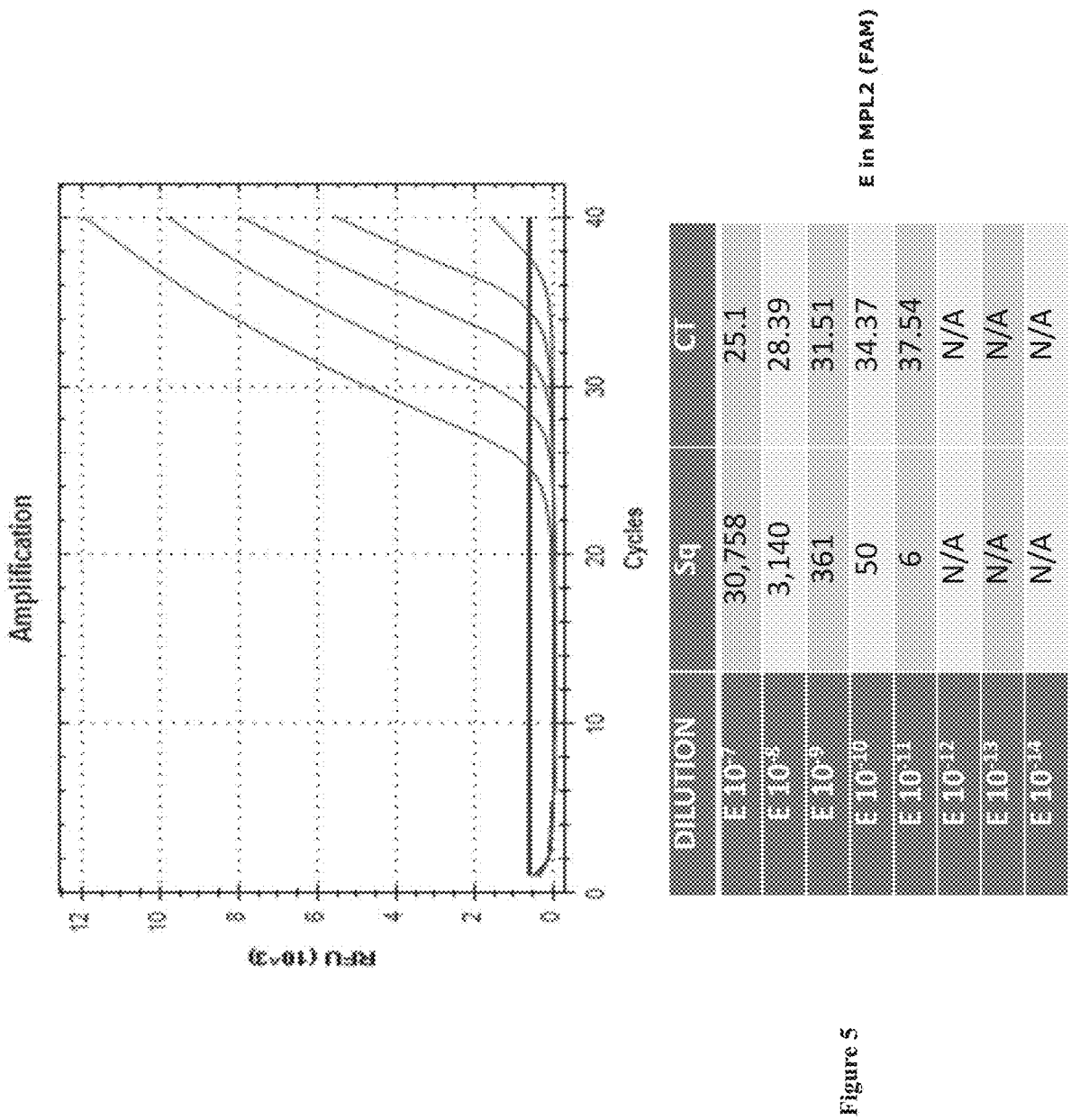
FIG. 5 shows a diagram illustrating the sensitivity of the rRT-PCR step for the detection of the E gene of SARS-CoV and SAR-CoV-2, in accordance with the invention.
Figure 6:
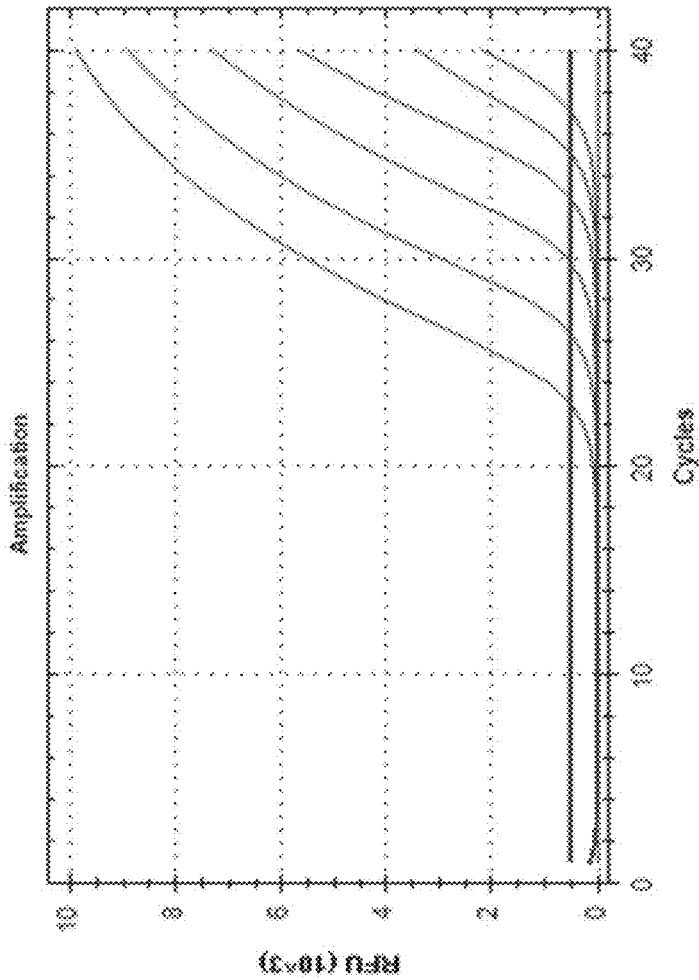
FIG. 6 shows a diagram illustrating the sensitivity of the rRT-PCR step for the detection of the upE gene of MERS-CoV, in accordance with the invention.
Figure 7:
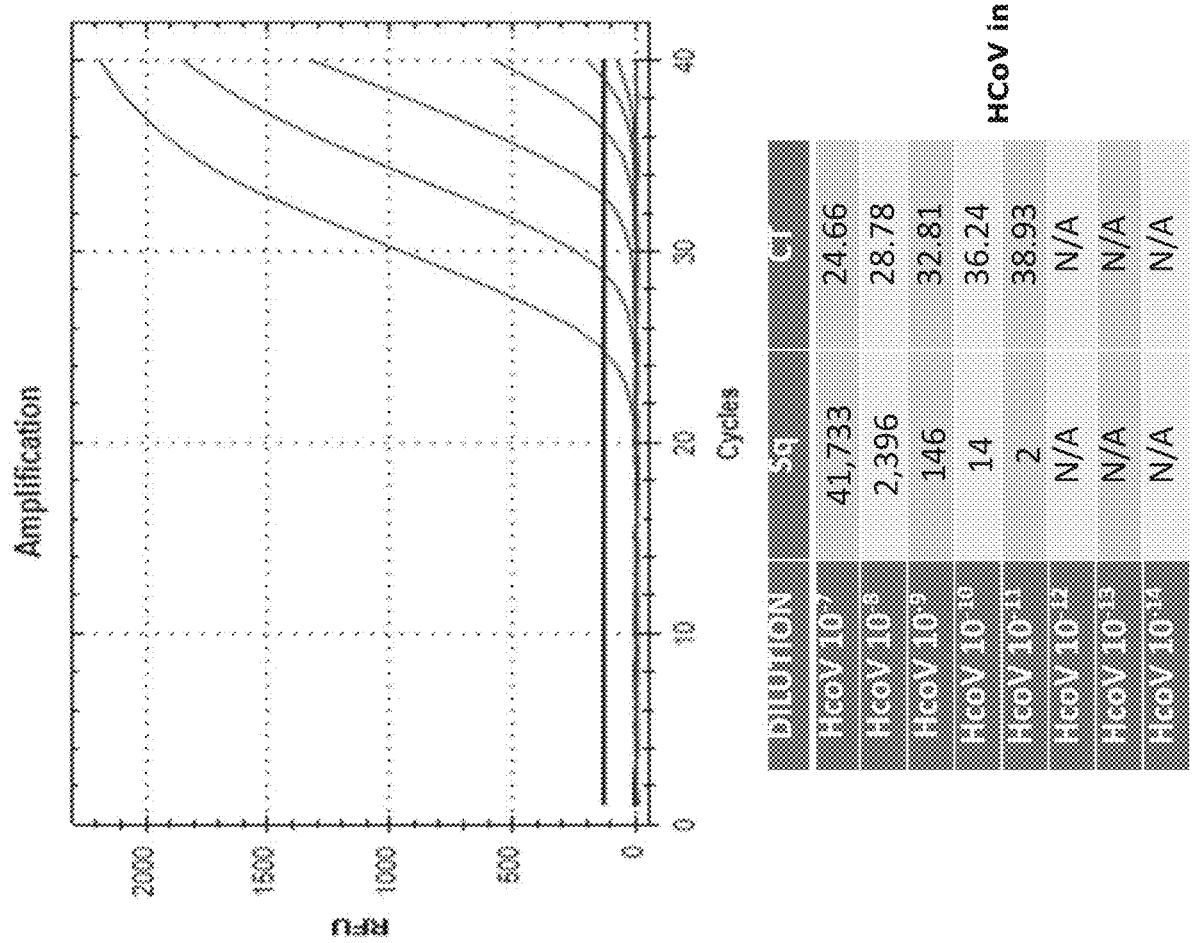
FIG. 7 shows a diagram illustrating the sensitivity of the rRT-PCR step for the detection of the gene of HCoV (CY5).

With reference to the above-listed figures, in the first one it is schematically shown how the virus binds to the target with its spike proteins on its surface and uses it as anchorage. The surface protein targets the ACE2 cell receptor and enters into the cells by using a special enzyme (TMPRSS2); once the virion has quietly settled, it releases its RNA.

The DNA apparatus of the host cells is then used for producing virion proteins that are used for replicating more infectious RNA. Proteins and RNA are used in the Golgi apparatus in order to produce more virus that can be released outside.

The viral load, given by the number of viral particles that are actively present in an organism, is linked to a highly unfavourable prognosis in elderly, allergic and immunocompromised patients. The early phases of the infection are often asymptomatic, and the early clinical symptoms might be easily mistaken for common cold disease symptoms. Tests have shown the ability of the virus to contaminate cells and tissues elsewhere in the body, such as guts, liver, stomach and kidneys. A recent report has shown SARS-CoV-2 RNA in a stool specimen, alerting on a new possible route of viral infection via the faecal-oral-gastrointestinal tract. In addition, the incubation period may take several days before the disease is fully manifested. It is not rare to encounter people becoming entirely symptomatic 10 to 15 days after the first exposure.

DNA positive controls were obtained from synthesized fragments of targeted DNA, specifically created for real-time PCR.

The main intent of using positive controls N1-C[+], N2-C[+], N3-C[+], E-C[+], upE-C[+], HCoV-C[+] and PEDV-C[+] was to exactly evaluate the grade of sensitivity in the amplification of the targeted DNA.

The sequences of these C[+] were synthesized by Integrated DNA Technologies (IDT) on a scale of 100 nM. An internal control targeting Ribonuclease P (RNase P-RP) is needed to verify that nucleic acid is present in every sample and is used for every sample to be processed. This also serves as extraction control to ensure that samples resulting as negative contain nucleic acid for testing.

For RNA extraction, a kit named $^{NK}$DNA-RNAprep-COLUMN for 50 preparations (supplied by Nam Khoa Biotek, Hồ Chí Minh, Vietnam) was used, which includes a spin column, a proteinase K ready for use, a binding buffer solution, a first washing buffer solution, a second washing buffer solution, a third washing buffer solution, and elution buffer.

Materials

The following components and products were used for the tests.

Clinical sputum specimens from individuals suspected of SARS-CoV/SARS-CoV-2 were taken in the course of 2020 at the University Pham Chau Trinh, Danang City (VIETNAM).

Two multiplex (MPL) rRT-PCR master mixes, MLP1 and MLP2, were prepared with the reagents and methods listed in Table I (Applied Biosystems, Thermo-Fisher, Hillsboro, Oregon USA).

The test used three sets of primers and probes to detect 3 regions in the SARS-CoV-2 nucleocapsid (N1-F,R,P; N2-F, R,P; N3-F,R,P), 1 region in the SARS-CoV upE (E-F1,R2, P1) gene, 1 region in the MERS-CoV HKU (HKURP-1F, RP-1R, RP-1Pr) gene, 1 region in the PDV-Virus N (NF, NR, PR) gene; the test used a set of primers and probes to detect human RNase P (RP) in clinical samples. RNA isolated from respiratory specimens was reverse transcribed to cDNA and subsequently amplified using AgPath-ID™ One-Step RT PCR (Applied Biosystems, Thermo-Fisher, Hillsboro, Oregon USA).

During the amplification process, the probes were annealed to the specific target sequence located between the forward and reverse primers. During the extension phase of the PCR cycle, the 5' nuclease activity of Taq polymerase (Applied Biosystems, Thermo-Fisher, Hillsboro, Oregon USA) degrades the bound probe, causing the reporter dye (FAM/HEX/TexasRED/CY5) to separate from the quencher dye (BHQ1/BHQ2/BHQ3), thereby generating a fluorescent signal. Fluorescence intensity is monitored for each rRT-PCR by CFX 96 (Biorad, Hercules, California USA).

TABLE I

Formula for preparing the multiplex rRT-PCR master mix.

| MPL1 rRT-PCR master mix | MPL2 rRT-PCR master mix | Amount (pm) per 1 reaction | Stock (pm/μl) | Volume (μl) per 100 reactions |
|---|---|---|---|---|
| 2019-nCoV_N1-F | E_Sarbeco_F1 | 10 | 100 | 10 |
| 2019-nCoV_N1-R | E_Sarbeco_R2 | 10 | 100 | 10 |
| 2019-nCoV_N1-P (FAM/BHQ1) | E_Sarbeco_P1 (FAM/BHQ1) | 5 | 100 | 5 |
| 2019-nCoV_N2-F | upE_TqF | 10 | 100 | 10 |
| 2019-nCoV_N2-R | upE_tqR | 10 | 100 | 10 |
| 2019-nCoV_N2-P (TexasRED/BHQ2)* | upE_TqPR (TexasRED/BHQ2) | 5 | 100 | 5 |
| 2019-nCoV_N3-F | PEDV-NF | 10 | 100 | 10 |
| 2019-nCoV_N3-R | PEDV-NR | 10 | 100 | 10 |
| 2019-nCoV_N3-P (HEX/BHQ1) | PEDV-PR (HEX/BHQ1) | 5 | 100 | 5 |
| RP-F | HCoV-HKU-1-F | 2 | 100 | 2 |
| RP-R | HCoV-HKU-1-Redit | 2 | 100 | 2 |
| RP-P (CY5/BHQ3) | HCoV-HKU-1-Pr (CY5/BHQ3) | 5 | 100 | 5 |
| Apath-ID RT-PCR buffer* | | 10 μl | | 1000 |
| Apath-ID RT-PCR enzyme* | | 0.8 μl | | 80 |
| Enzyme stabilizer* | | 1 μl | | 100 |
| DNAse/RNAse free DW | | to 15 μl | | 236 |
| Total | | 15 μl | | 1500 |

*The "path-ID RT-PCR buffer 2X", the "Apath-ID RT-PCR enzyme 25X" were from "AgPath-ID ™ One-Step RT-PCR" (Applied Biosystems-Thermo-Fisher, Hillsboro, Oregon, USA), Primers and Probes (IDT, Coralville, Iowa, USA). The "enzyme stabilizer" was supplied by Nam Khoa Co. Ltd. (Ho Chi Minh City-Vietnam) to stabilize the enzyme in the mix prepared for rRT-PCR.

The MPL1 phase was implemented for detecting SARS-CoV-2 targets and searching for the presence of host epithelial cells in the samples; the MPL2 phase was used for detecting SARS-CoV, SARS-CoV-2, HCoV, MERS-CoV, and also as a control for the recognition of the integral coronavirus (PEDV).

The prepared multiplexes MPL1 and MPL2 were shared in test tubes, and each one received 120 μl for a total of 8 mixes per PCR (15 μl/mix) and was stored at −20° C. until used.

The primers and probes listed in Tables II-III-IV were used for preparing the MPL1-2 master mixes for rRT-PCR. These primers and probes were synthesized by IDT (Singapore and USA) on a scale of 100 nM.

TABLE II

Primers and probes used for preparing the rRT-PCR master mix.

| Name | Target gene | Reference |
|---|---|---|
| 2019-nCoV_N1-F | N1 | From: 2019-Novel Coronavirus (2019-nCoV) |
| 2019-nCoV_N1-R | (SARS-CoV-2) | rRT-PCR Panel Primers and Probes. Center for |
| 2019-nCoV_N1-P (FAM/BHQ1) | | Diseases and Control (CDC) USA. |
| 2019-nCoV_N2-F | N2 | |
| 2019-nCoV_N2-R | (SARS-CoV-2) | |
| 2019-nCoV_N2-P (TexasRED/BHQ2) | | |
| 2019-nCoV_N3-F | N3 | |
| 2019-nCoV_N3-R | (SARS-CoV-2) | |
| 2019-nCoV_N3-P (HEX/BHQ1) | | |
| E_Sarbeco_F1 | E | Diagnostic detection of 2019-nCoV by rRT-PCR |
| E_Sarbeco_R2 | (SARS-CoV & | Corman et al. |
| E_Sarbeco_P1 (FAM/BHQ1) | SARS-CoV-2) | |

TABLE II-continued

Primers and probes used for preparing the rRT-PCR master mix.

| Name | Target gene | Reference |
|---|---|---|
| upE_TqF<br>upE_tqR<br>upE_TqPR (TexasRED/BHQ2) | upE<br>(MERS-CoV) | Diagnostic detection of 2019-nCoV by rRT-PCR Corman et al. |
| HCoV-HKU-1-F<br>HCoV-HKU-1-Redit<br>HCoV-HKU-1-Pr (CY5/BHQ3) | Replicase<br>(HCoV) | From: R. Rockett, |
| RP-F<br>RP-R<br>RP-P (CY5/BHQ3) | RNAseP<br>(human) | From: 2019-Novel Coronavirus (2019-nCoV) rRT-PCR Panel Primers and Probes. Center for Diseases and Control (CDC) USA. |
| PEDV-NF<br>PEDV-NR<br>PEDV-PR (HEX/BHQ1) | N<br>(PEDV*) | From: Yu et al. |

*PEDV Porcine Epidemic Diarrhoea virus.

TABLE III

MPL1 sequence of primers and probes used for preparing the rRT-PCR master mix.

| Name | Sequence | SEQ ID |
|---|---|---|
| N1-F2019-nCoV | GACCCCAAAATCAGCGAAAT | SEQ ID NO: 1 |
| N1-R2019-nCoV | TCTGGTTACTGCCAGTTGAATCTG | SEQ ID NO: 2 |
| N1Probe | FAM-ACCCCGCATTACGTTTGGTGGACC-BHQ1 | SEQ ID NO: 3 |
| N2-F2019-nCoV | TTACAAACATTGGCCGCAAA | SEQ ID NO: 4 |
| N2-R2019-nCoV | GCGCGACATTCCGAAGAA | SEQ ID NO: 5 |
| N2Probe | TexasRED-ACAATTTGCCCCCAGCGCTTCAG-BHQ2 | SEQ ID NO: 6 |
| N3-F2019-nCoV | GGGAGCCTTGAATACACCAAAA | SEQ ID NO: 7 |
| N3-R2019-nCoV | TGTAGCACGATTGCAGCATTG | SEQ ID NO: 8 |
| N3Probe | HEX-AYCACATTGGCACCCGCAATCCTG-BHQ1 | SEQ ID NO: 9 |
| RP-F | AGATTTGGACCTGCGAGCG | SEQ ID NO: 10 |
| RP-R | GAGCGGCTGTCTCCACAAGT | SEQ ID NO: 11 |
| RP-P | CY5-TTCTGACCTGAAGGCTCTGCGCG-BHQ3 | SEQ ID NO: 12 |

TABLE IV

MPL2 sequence of primers and probes used for preparing the rRT-PCR master mix.

| Name | Sequence | SEQ ID |
|---|---|---|
| E_Sarbeco_F1 | ACAGGTACGTTAATAGTTAATAGCGT | SEQ ID NO: 13 |
| E_Sarbeco_R2 | ATATTGCAGCAGTACGCACACA | SEQ ID NO: 14 |
| E_Sarbeco_P1 | ACACTAGCCATCCTTACTGCGCTTCG-BHQ1 | SEQ ID NO: 15 |
| PEDVNEedit3 | GCGCAAAGACTGAACCCACTA | SEQ ID NO: 16 |
| PEDVNR | TTGCCTCTGTTGTTACTTGGAGAT | SEQ ID NO: 17 |
| PEDV-HEX(RV) | HEX-TGTTGCCATTGCCACGACTCCTGC-BHQI | SEQ ID NO: 18 |
| upE_TqF | GCAACGCGCGATTCAGTT | SEQ ID NO: 19 |
| upE_tqR | GCCTCTACACGGGACCCATA | SEQ ID NO: 20 |
| upE_TqPR (TexasRED) | TexasRED-CTCTTCACATAATCGCCCCGAGCTCG-BHQ2 | SEQ ID NO: 21 |
| HCoV-HKU-1-F | CCTTGCGAATGAATGTGCT | SEQ ID NO: 22 |
| HCoV-HKU-1-R | TTGCATCACCACTGCTAGTACCAC | SEQ ID NO: 23 |
| HCoV-HKU-1-PR | CY5-TGTGTGGCGGTTGCTATTATGTTAAGCCTG-BHQ3 | SEQ ID NO: 24 |

Positive Controls

DNA positive controls were obtained from synthesized fragments of targeted DNA specially created for the rRT-PCR analysis. The positive controls N1-C[+], N2-C[+], N3-C[+], E-C[+], upE-C[+], HCoV-C[+] and PEDV-C[+] were used to test the sensitivity in the amplification of the target DNA. The sequences of these C[+] were synthesized by IDT on a scale of 100 nM. All DNA positive controls were prepared in the stock solution of 100 pm/µl and then diluted to the working solution of 10 mM Tris: 0.1 mM EDTA; pH 8.0 to obtain a final solution of TE 1×(10 fm/µl). All DNA positive controls were shared in a low-binding Eppendorf tube (Eppendorf, Hamburg, Germany) having a volume of 200 µl/each, and kept at −20° C. until used.

PEDV C[+] is a positive control acting as an internal control for its ability to detect the real coronavirus in the samples. A lyophilized product was used, stored at −20° C. It was diluted into 200 µl of TE 1×, then aliquoted into 20 µl and stored at −20° C.

The RNA extraction kit included the spin column, a proteinase K ready for use, binding buffer, a first washing buffer, a second washing buffer, a third washing buffer, and elution buffer. This kit was supplied by NKDNARNAprep-COLUMN for 50 preparations (Nam Khoa Co. LTD, Hồ Chí Minh, Vietnam), stored at room temperature.

The thermal cycle was set up in the Real Time PCR (rRT-PCR) machine as follows: 1 cycle at 45° C. for 10 minutes; 1 cycle at 95° C. for 10 minutes; and 40 cycles at 95° C. for 15 seconds and at 60° C. for 1 minute. Four channels were also selected: FAM, HEX, TexasRED and CY5.

Methods and Results

As far as the in-vitro sensitivity of the MPL rRT-PCR mix is concerned, the procedure was based on the use of 3 tubes of MPL1 master mix and 3 tubes of MPL2 master mix (0.1 ml each) to be inserted into rRT-PCR and then thawed at room temperature.

The tubes were finally shaken up and down 8-10 times; at the end of each rRT-PCR, the master mix was shared into 24 0.1 ml low-profile white PCR tubes (Eppendorf, Hamburg, Germany) and stored in a cold environment.

A 10× dilution gradient of the DNA positive controls was prepared, then 5 µl of each dilution between 10-7 and 10-14 were added to the MPL rRT-PCR mix. MPL1 received N1-C[+], N2-C[+], N3-C[+], N1-C[+]. For MPL2, E-C[+], upE-C[+], HCoV-C[+] were added. The PCR tubes were closed and moved into the CFX-96 thermal cycler for the procedure.

The results are shown in FIGS. 2 to 7.

The sensitivity of the rRT-PCR step for the detection of all coronavirus target genes is summarized in the following Table V.

TABLE V

Limit of detection (LOD) of the DNA positive controls for verifying the sensitivity of the rRT-PCR step of the test.

| | N1 SARS-CoV-2 | N2 SARS-CoV-2 | N3 SARS-CoV-2 | E gene SARS-CoV | upE gene MERS-CoV | Replicase HCoV |
|---|---|---|---|---|---|---|
| LOD in reaction volume (Copies number) | 3 | 8 | 3 | 6 | 14 | 2 |

As concerns the in-vitro sensitivity of the Multiplex polymerase chain reaction (MPL in rRT-PCR) for the detection of the intact coronavirus in the sputum sample, the following should be considered.

Two tubes of MPL1 and MPL2 rRt-PCR master mixes were thawed at room temperature. The samples were strongly shaken about 8-10 times and let lay for a few instants, then shared into 8 0.1 (low-profile white) PCR tubes. The MPL rRT-PCR mix was kept in a cold environment. The lyophilized PEDV was rehydrated with 200 µl of TE 1×, mixed well and diluted (ten-fold dilution) in TE 1× from 10-6 to 10-13.

Each 20 µl dilution was added into 200 µl of sputum. The sputum was stored in the laboratory after routinely bacterial examination.

RNA extraction from the sputum was carried out by using the NKDNARNA prep-COLUMN kit (Nam Khoa LTD, Hồ Chí Minh, Vietnam) in accordance with the kit instructions. 5 µl of each RNA extracted were added into one MPL1 real-time PCR mix and one MPL2 real-time PCR mix.

Figure 8:
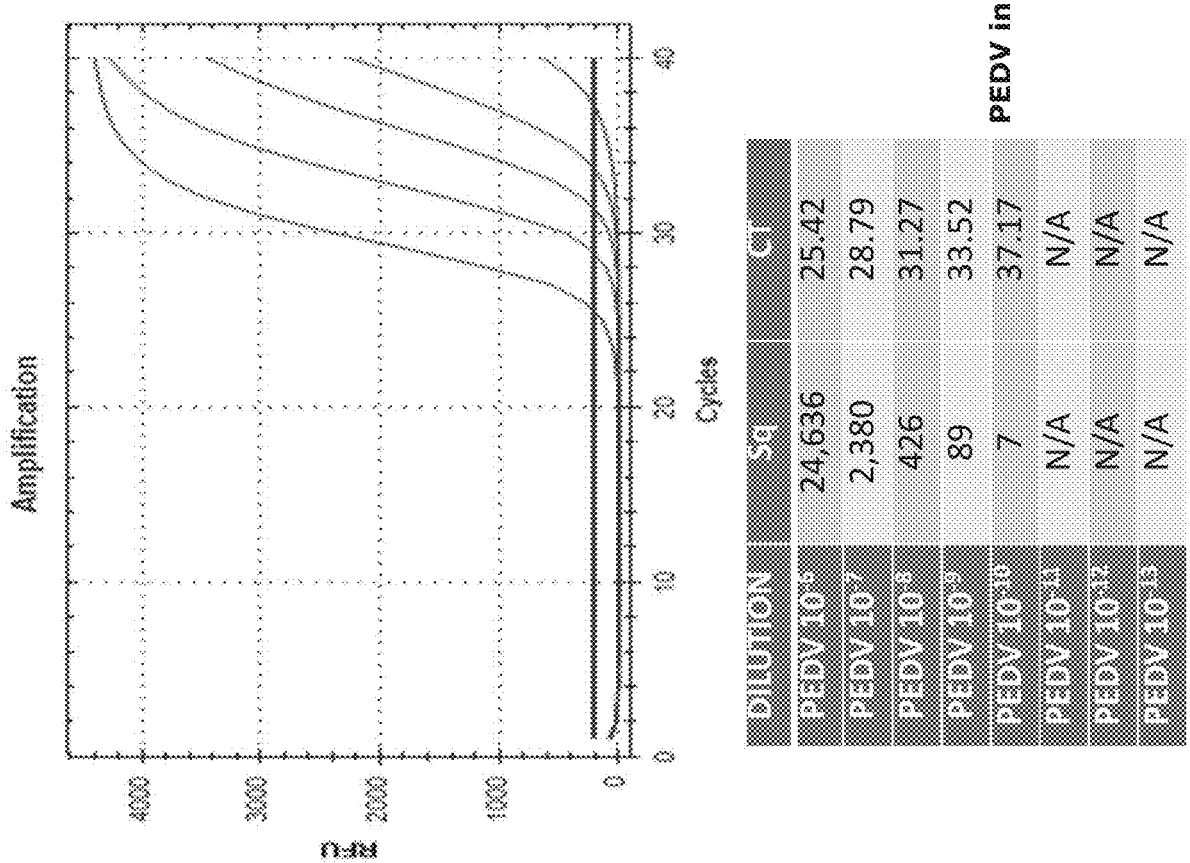
FIG. 8 shows a diagram illustrating the rRT-PCR sensitivity for the detection of the intact Coronavirus from the sputum sample.
Figure 9:
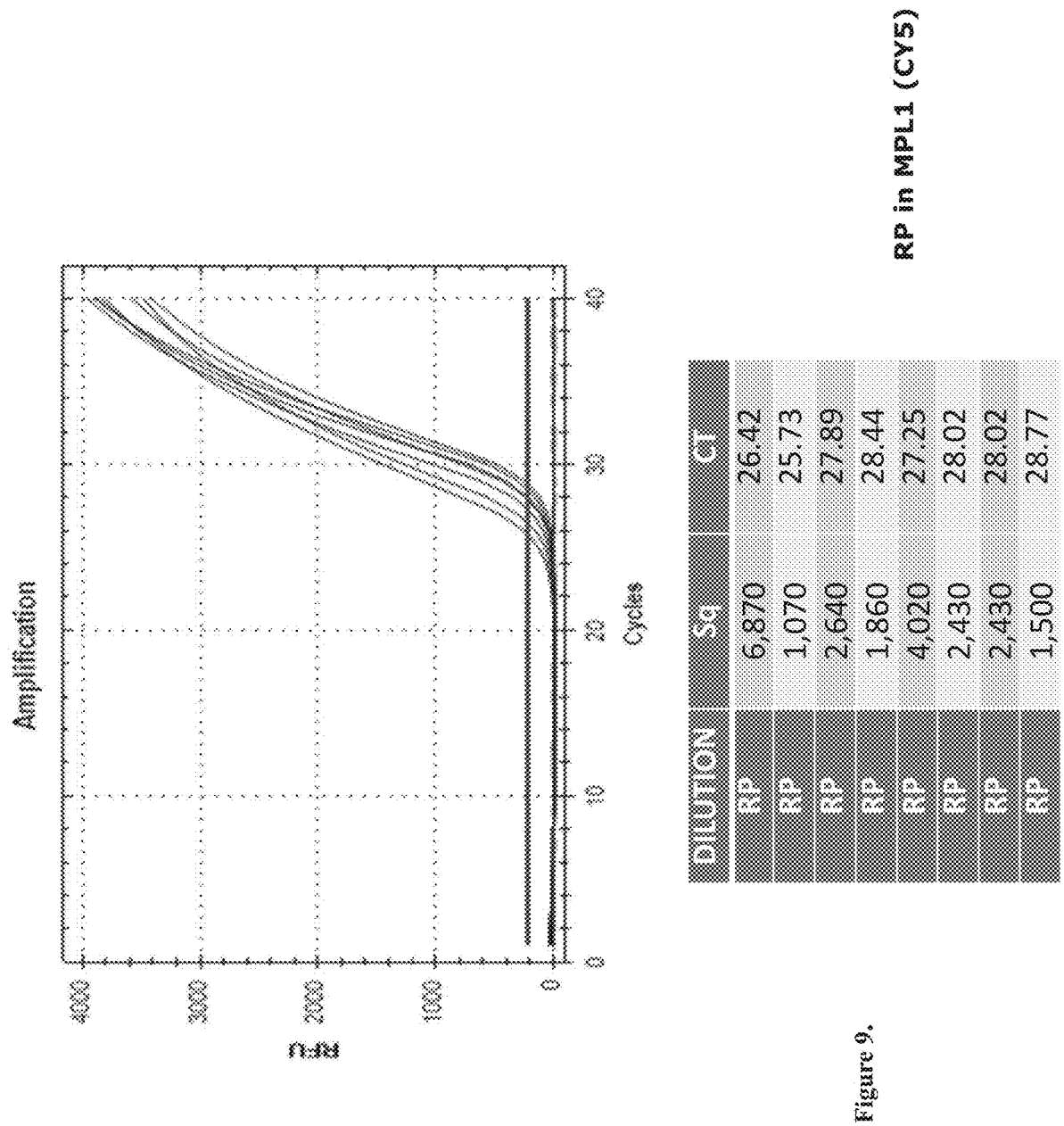
FIG. 9 shows a diagram illustrating all the RNAseP genes detected in MPL1.

Subsequently, all tubes were put into the CFX-96 thermal cycler, and then processed (FIGS. 8 and 9).

For what concerns the protocol for detecting SARS-CoV-2, SARS-CoV, MERS-CoV and HCoV in the sample, we proceeded as follows:

The analysed specimens were collected from sputum, throat swab and post-nasal swab. In the acute phase, blood plasma could also be collected in ethylenediaminetetraacetic acid (EDTA) containers, useful for plasma isolation. The samples were kept at 4° C. for up to 48 hours or at −70° C. for longer periods of storage as necessary.

For the throat and post-nasal specimens, the swab was eluted in TE 1× in order to obtain 200 µl. The same procedure was performed with plasma. Each plasma sample was thus eluted in TE 1× in order to obtain 200 µl. The sputum specimen was homogenized at a 1:1 ratio, i.e. 1 volume of sputum for 1 volume of TE 1×, centrifuged for 15 seconds, and then collected. Then, 20 µl of PEDV C [+] were added into 200 µl of sample prepared with extra 20 µl of proteinase K at 56° C. for 15 minutes. At the end of the 15 minutes, the sample was ready for RNA extraction using the NKDNA RNAprep-COLUMN kit in accordance with the kit instructions.

The Multiplex (PCR MPL) master mix was melted at room temperature and mixed by shaking it up and down several times for 15 seconds. The master mix was then poured into a PCR tube (15 µl/mix) and kept in a cold place. The RNA was added to the extracted samples together with DNA C[+] and TE 1× as negative controls and inserted into the rRT-PCR mix (5 µl for each real-time PCR mix as indicated in Table VI). The PCR tubes were inserted into the CFX-96 thermal cycler.

TABLE VI

Insertion of RNA extracted samples (2 samples), DNA C [+] , negative control into the MPL rRT-PCR mix.

| PCR tube | 1 | 2 | 3 | 4 | 5 | 6 | 7 | 8 |
|---|---|---|---|---|---|---|---|---|
| MPL1 (µl) | | | | | 15 | | 15 | 15 |
| MPL2 (µl) | | 15 | | 15 | | 15 | | 15 |
| S1 RNA extracted (µl) | 5 | | 5 | | | | | |
| S2 RNA extracted (µl) | | 5 | | 5 | | | | |
| DNA-C[+]1* (µl) | | | | | 5 | | | |
| DNA-C[+]2** (µl) | | | | | | 5 | | |
| TE 1X (µl) | | | | | | | 5 | 5 |
| Total volume | 20 | 20 | 20 | 20 | 20 | 20 | 20 | 20 |

*DNA-C[+] 1 is the mix of N1-C[+], N2-C[+], N3-C[+];
**DNA-C[+] 2 is the mix of E-C[+], PEDV-C[+], upE-C[+], HCoV-C[+].

The negative controls were not amplified (FIG. 10). These results indicated that the samples had not been contaminated.

For the positive control, on the other hand, in the MPL1 Multiplex C[+]1 had amplification in the FAM (N1), TexasRED (N2) and HEX (N3) channels. In MPL2, C[+]2 had amplification in the FAM (E), TexasRED (upE), HEX (PEDV) and CY5 (HCoV) channels. This result indicated that the amplification step is sensitive in the detection of all target DNA.

Figure 11:
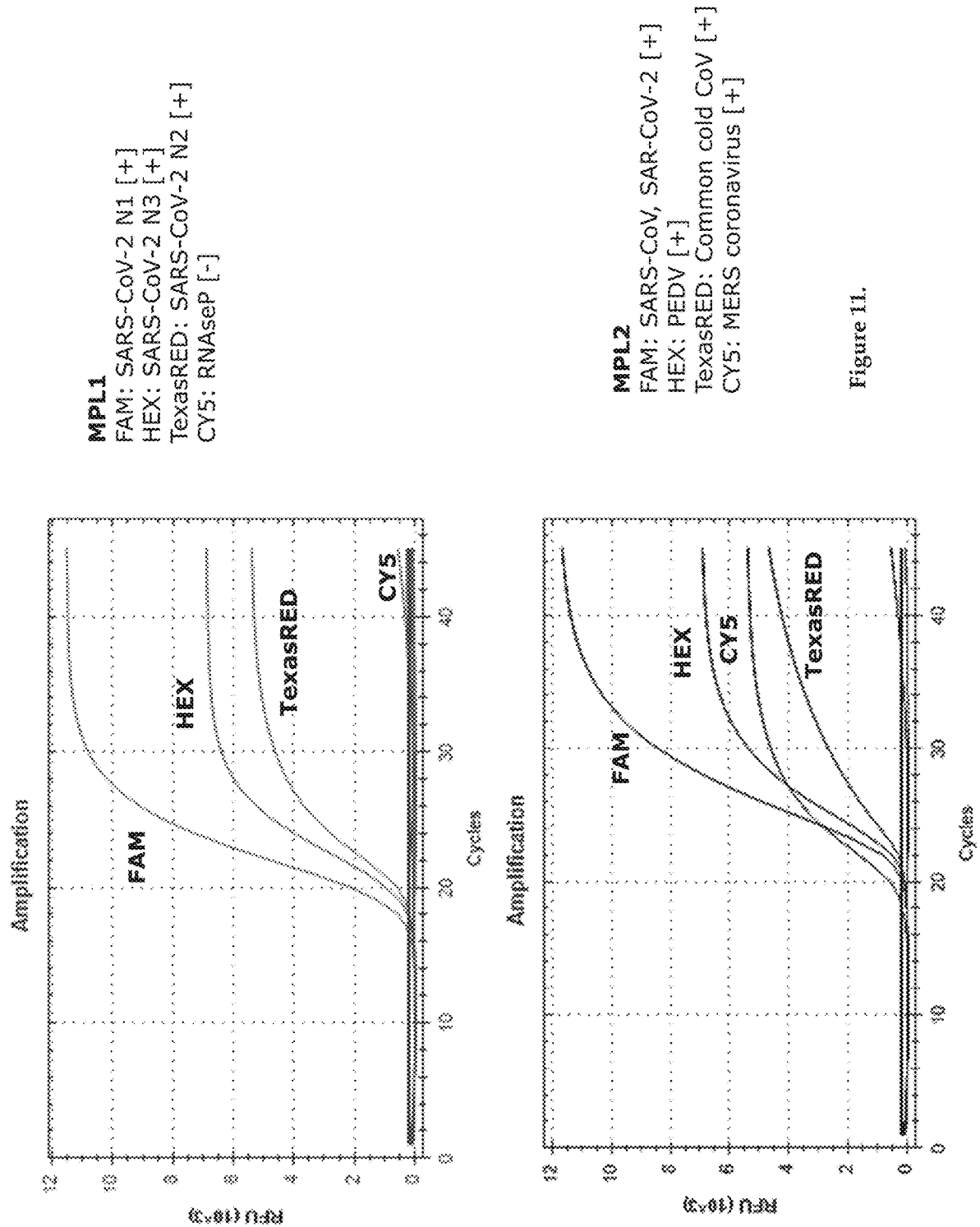
FIG. 11 shows diagrams wherein the positive control shows the amplification signal of FAM (N1), TexasRED (N2), HEX (N3) in MPL1 and FAM (E), HEX (PEDV), TexasRED (upE), CY5 (HCoV) in MPL2.

The situation is shown in FIG. 11, which shows that the positive control shows the amplification signal of FAM (N1), TexasRED (N2), HEX (N3) in MPL1 and FAM (E), HEX (PEDV), TexasRED (upE), CY5 (HCoV) in MPL2;

For what concerns the negative results of SARS-CoV-2, SARS-CoV, MERS-CoV and HCoV, the target DNA pathogens were not amplified.

Figure 12:
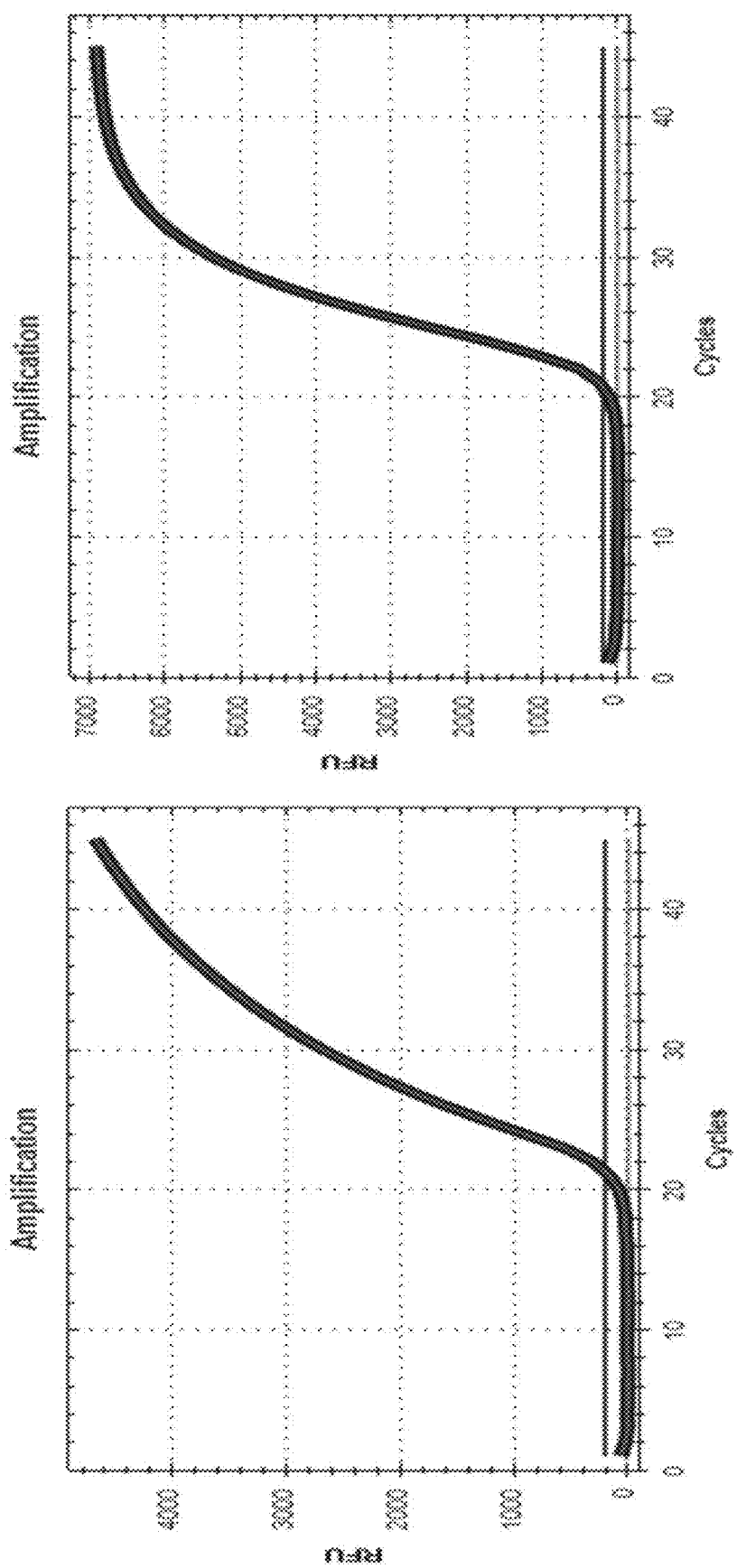
FIG. 12 shows diagrams illustrating negative samples with every coronavirus pathogen, which indicated no amplification of all the related target genes. This result is not false negative, the MLP1 must have the amplification of RP gene (CY5) of the host epithelial cell and the MLP2 must have the amplification of the internal control in the PEDV.

However, in MPL1 the RP (CY5) was amplified to detect the presence of epithelial cells of the patient. MPL2 PEDV (HEX) was amplified to confirm that the kit could extract RNA of the intact coronavirus with the rRT-PCR amplification procedure. These MLP1 and MLP2 procedures confirmed the ability to exclude false negatives as indicated in FIG. 12.

The latter shows that the samples negative for every coronavirus pathogen indicated no amplification of all related target genes. This result is not a false negative, in that MLP1 must have the amplification of the RP gene (CY5) of the host epithelial cell and MLP2 must have the amplification of the internal control in the PEDV.

In regard to the samples that turned out positive to SARS-CoV-2, in MPL1 all target genes N1, N2, N3 of SARS-CoV-2 were amplified in the FAM (N1), TexasRED (N2) and HEX (N3) channels, respectively. Amplification of RP (CY5) of the host epithelial cells may be present, even though this datum is strictly dependent on the number of specimens collected.

Figure 13:
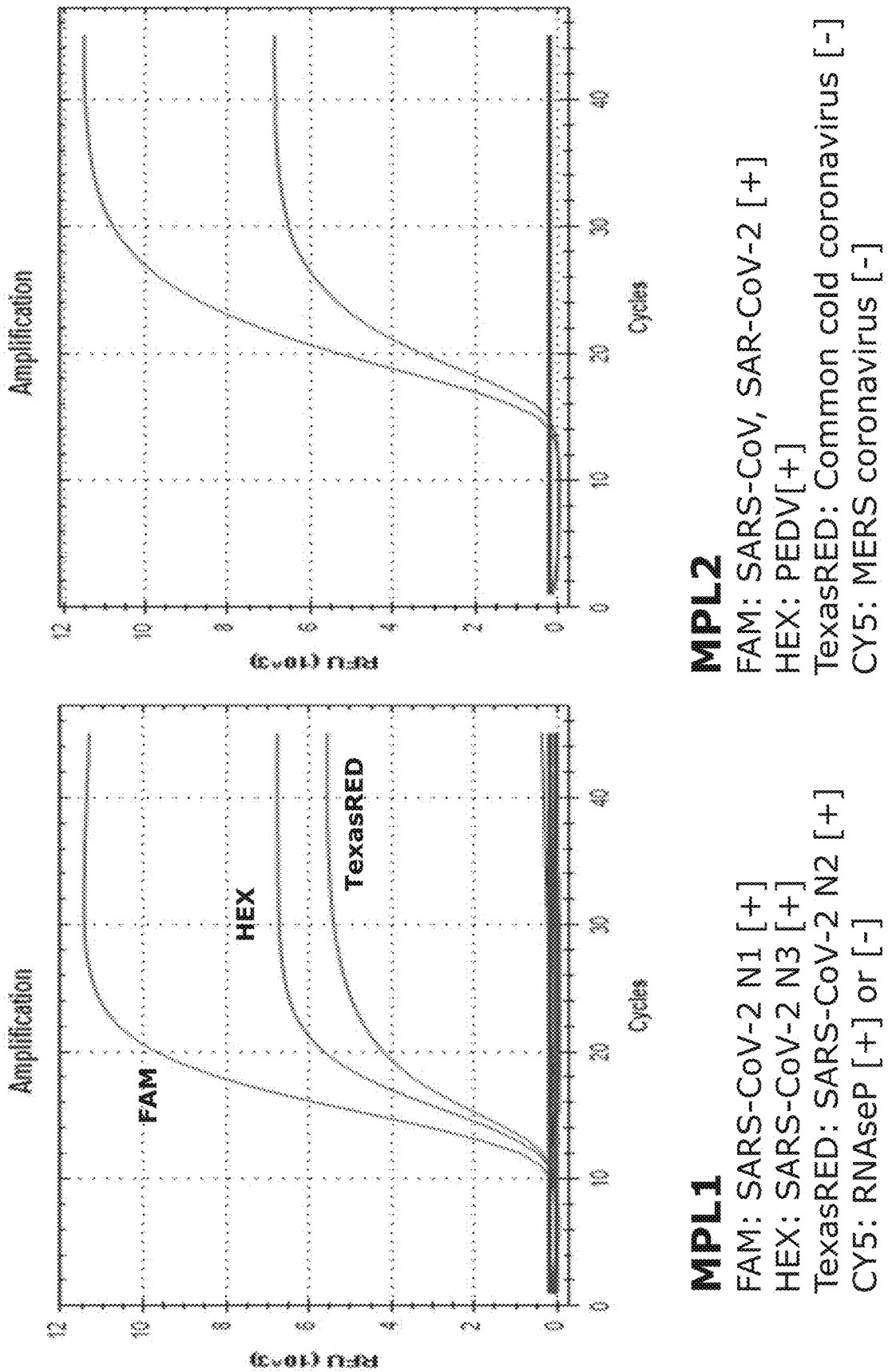
FIG. 13 shows diagrams illustrating samples positive for SARS-CoV-2 with all the target genes of the coronavirus pathogens, among which N1 (FAM), N2 (TexasRED), N3 (HEX) and E (FAM) were amplified in MPL1, while in MPL2 the N gene (HEX) of PEDV was also amplified.

In MPL2, the E gene (FAM) of SARS-CoV and SARS-CoV-2 and the N gene (HEX) of PEDV were amplified. The results are shown in FIG. 13.

As can be seen, in the samples positive for SARS-CoV-2 all target genes of the coronavirus pathogens, including N1 (FAM), N2 (TexasRED), N3 (HEX) and E (FAM) were amplified in MPL1. In MPL2 also the N gene (HEX) of PEDV was amplified.

Figure 14:
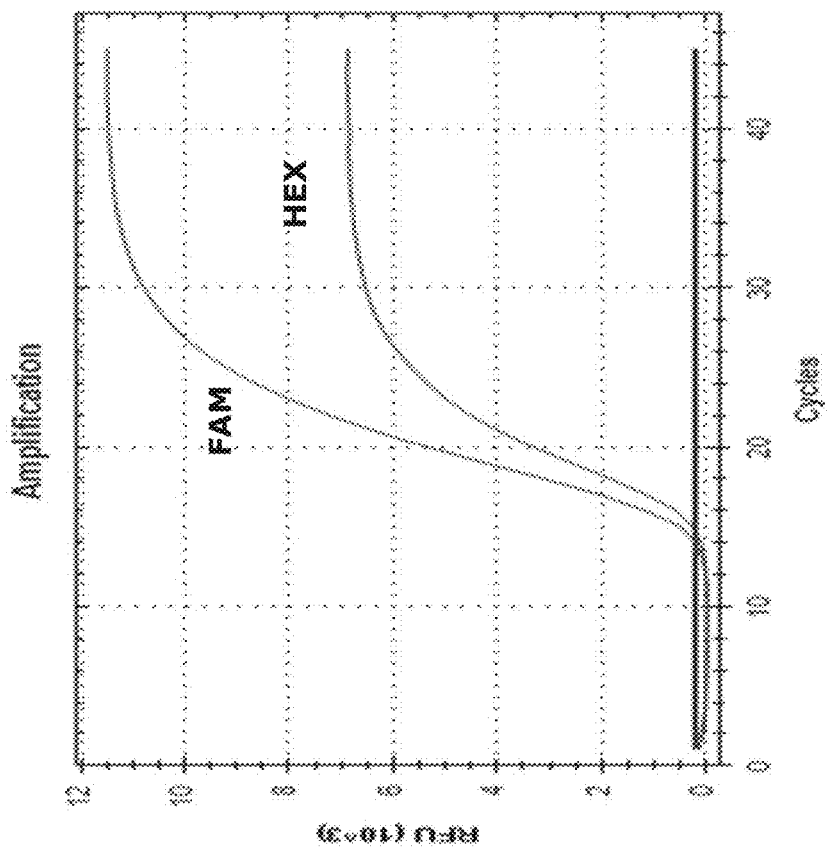
FIG. 14 shows diagrams illustrating samples positive for SARS-CoV that showed no amplification of the target genes of SARS-CoV-2, N1 (FAM), N2 (TexasRED), N3 (HEX) in MPL1; wherein the SARS-CoV and SARS-CoV-2 E gene (FAM) was amplified in MPL2; also, the N gene (HEX) of PEDV coronavirus was amplified in MPL2 and the RP gene (CY5) of the host epithelial cell was amplified in MPL1.
Figure 14:
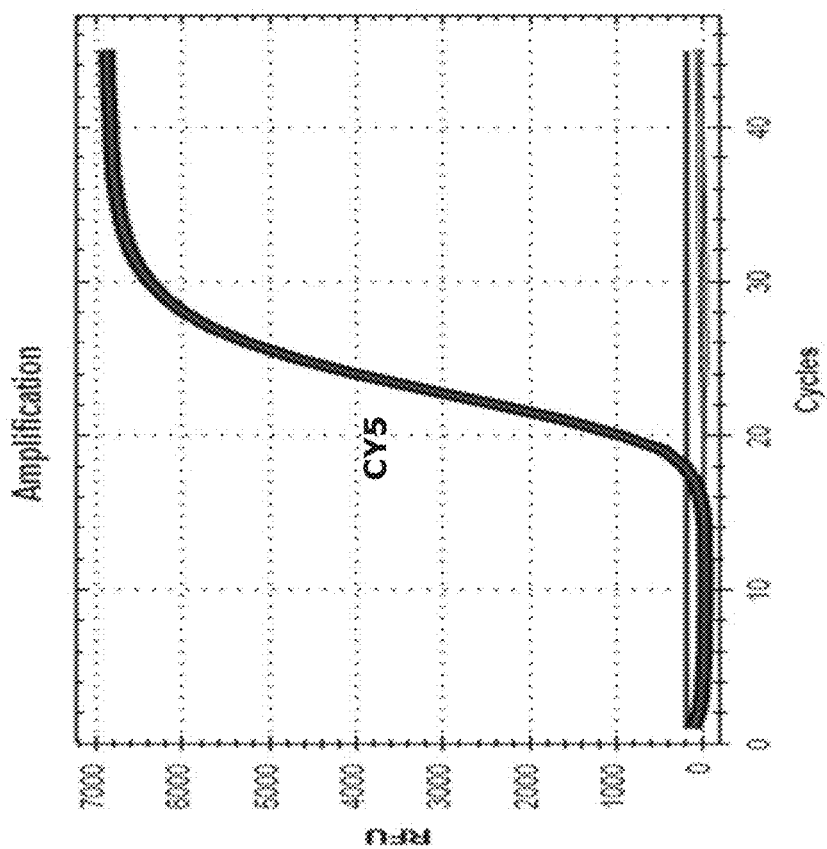

As concerns the samples that turned out positive to SARS-CoV, in MPL1 the RP gene of the epithelial cells was amplified. In MPL2, the E gene (FAM) of SARS-CoV and SAR-CoV-2 was amplified, and also the N gene (HEX) of PEDV was amplified, as shown in FIG. 14.

The latter shows SARS-CoV positive samples that showed no amplification of the target genes of SARS-CoV-2 N1 (FAM), N2 (TexasRED), N3 (HEX) in MPL1. The SARS-CoV and SARS-CoV-2 E gene (FAM) was amplified in MPL2. Also, the N gene (HEX) of PEDV coronavirus was amplified in MPL2 and the RP gene (CY5) of the host epithelial cell was amplified in MPL1.

Figure 15:
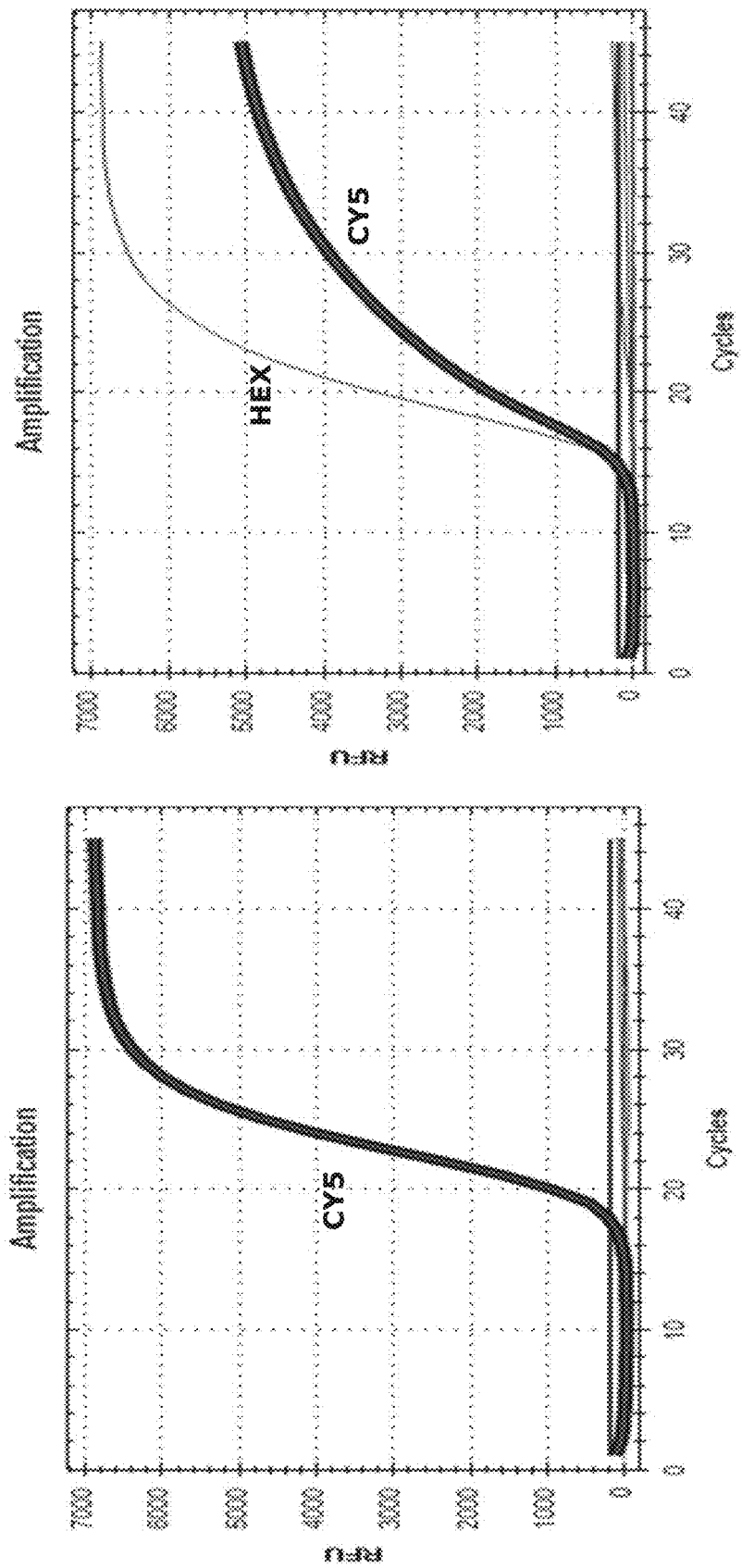
FIG. 15 shows diagrams illustrating samples positive for MERS-CoV indicated by the lack of amplification of all the target genes of SARS-CoV-2, including N1 (FAM), N2 (TexasRED), N3 (HEX) in MPL1, wherein the Ribonuclease P (RNase P-RP) (CY5) of the host epithelial cell was amplified; in MPL2 there was no amplification for the E gene (FAM) of SAR-CoV and SARS-CoV-2, as well as for the replicase gene (CY5) of HCoV, even though the upE gene (TexasRED) of MERS-CoV and the N gene (HEX) of PEDV coronavirus were amplified.

As concerns the samples that turned out positive to MERS-CoV in MPL1, the RP gene for the detection of the host epithelial cells was amplified in MPL2; the upE gene (TexasRED) of MERS-CoV and the N gene (HEX) of PEDV were amplified as indicated in FIG. 15.

In FIG. 15 the samples positive to MERS-CoV are indicated by the lack of amplification of all target genes of SARS-CoV-2 including N1 (FAM), N2 (TexasRED), N3 (HEX) in MPL1; the RP (CY5) of the host epithelial cell was amplified. In MPL2 there was no amplification for the E gene (FAM) of SAR-CoV and SARS-CoV-2, as well as for the replicase gene (CY5) of HCoV.

However, the upE gene (TexasRED) of MERS-CoV and the N gene (HEX) of PEDV coronavirus were amplified.

As regards the samples that turned out positive to HCoV, in MPL1 only the RP gene of the host epithelial cells was amplified. In MPL2 the replicase gene (CY5) of HCoV and the N gene (HEX) of PEDV were amplified.

Figure 16:
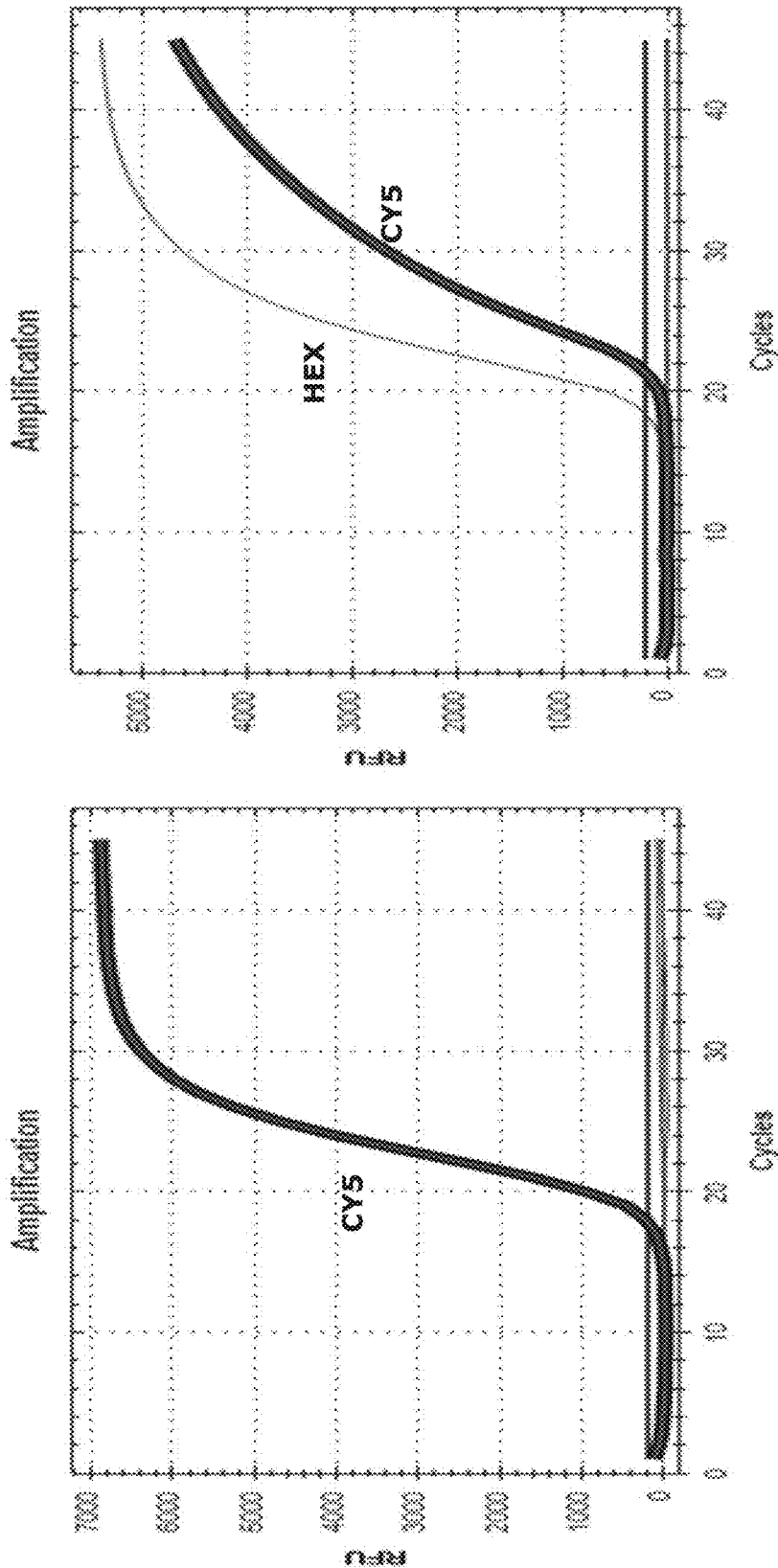
FIG. 16 shows diagrams illustrating samples positive for HCoV indicated without the amplification of all the target genes of SARS-CoV-2, including N1 (FAM), N2 (TexasRED), N3 (HEX) in MPL1, except for the RP (CY5) of the host epithelial cell, which was amplified; in MPL2, the E gene (FAM) of SAR-CoV and SARS-CoV-2 and the upE gene (TexasRED) of MERS-CoV were not amplified, even though the replicase gene (CY5) of HCoV and the N gene (HEX) of PEDV were amplified.

In the results shown in FIG. 16, the samples positive to HCoV are shown without amplification of all target genes of SARS-CoV-2 including N1 (FAM), N2 (TexasRED), N3 (HEX) in MPL1, except for the RP (CY5) of the host epithelial cell, which was amplified. In MPL2, the E gene (FAM) of SAR-CoV and SARS-CoV-2 and the upE gene (TexasRED) of MERS-CoV were not amplified. However, the replicase gene (CY5) of HCoV and the N gene (HEX) of PEDV were amplified.

It emerges from the above that the current positive results of the diagnostic test detect the presence of SARS-CoV-2 RNA, in that this procedure showed enough sensitivity and specificity to be potentially independent of the patient's clinical history and other diagnostic information in determining the patient's infection status.

Figure 17:
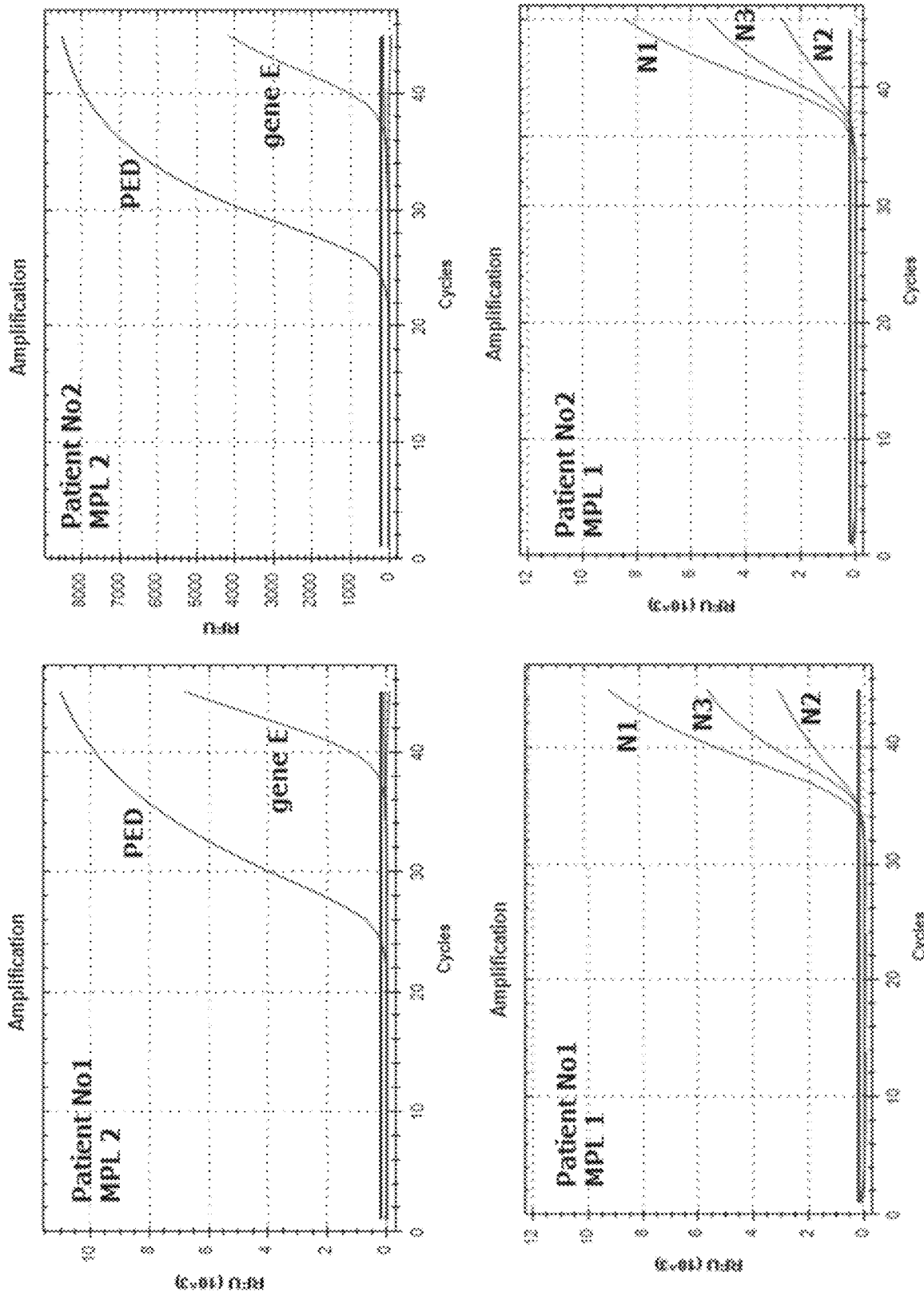
FIG. 17 shows diagrams of two RNAs extracted from 2 patients who were positive for SARS-CoV-2 (COVID-19), wherein the PEDV and E genes were amplified in each MPL2 of the patients (up left and right), while MPL1 of patients 1 and 2 showed amplification of the specific targets of the N1, N2 and N3 genes of COVID-19. The in vivo results determined a strong positive outcomes related to the SARS-CoV-2 presence.
Figure 18:
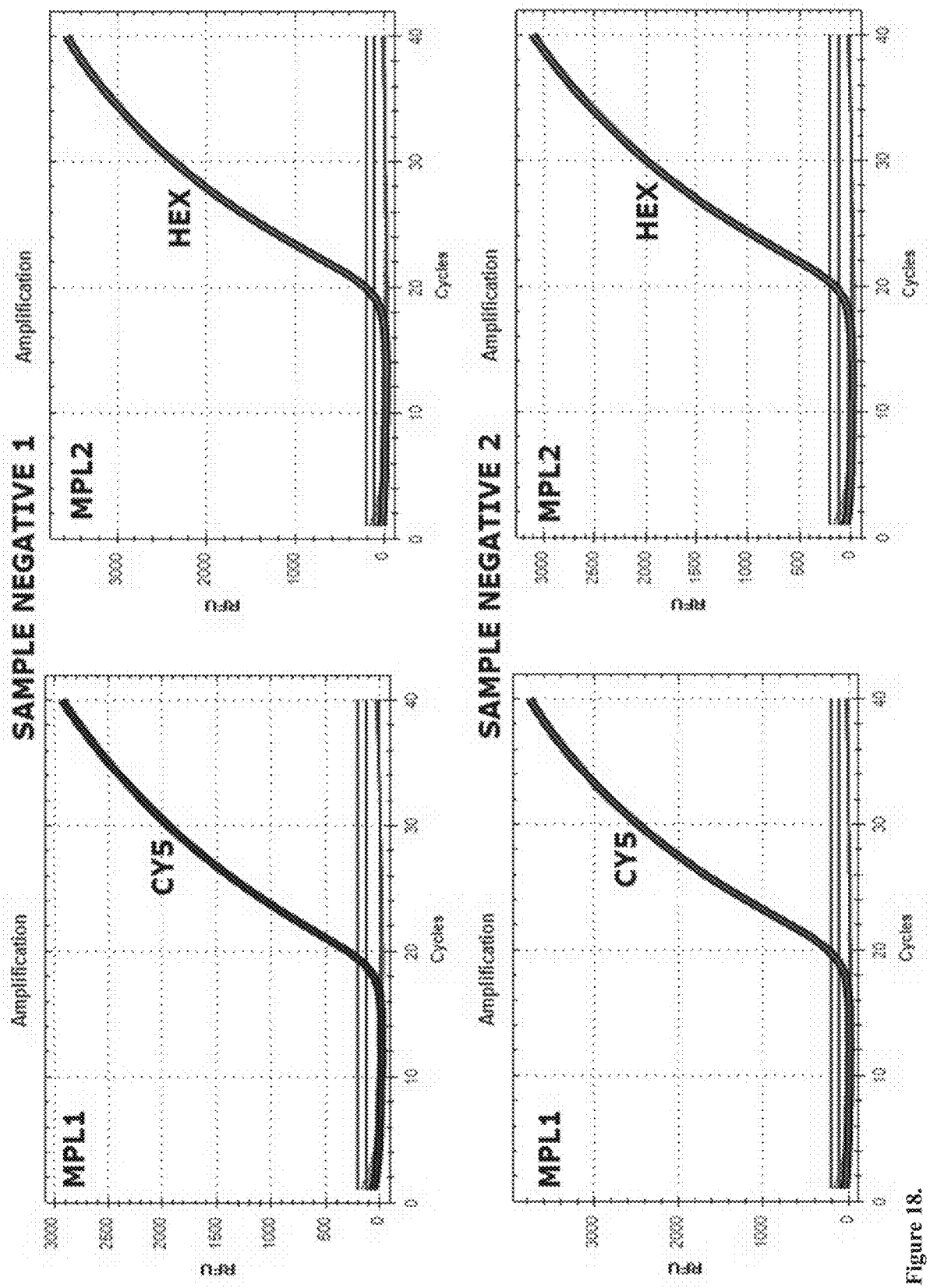
FIG. 18 shows diagrams of two RNAs extracted from 2 patients who were negative for SARS-CoV-2 (COVID-19), wherein MPL1 detected only the presence of host epithelial cells, while MPL2 detected only the presence of PEDV. This indicated these were real, not false negative results.
Figure 19:
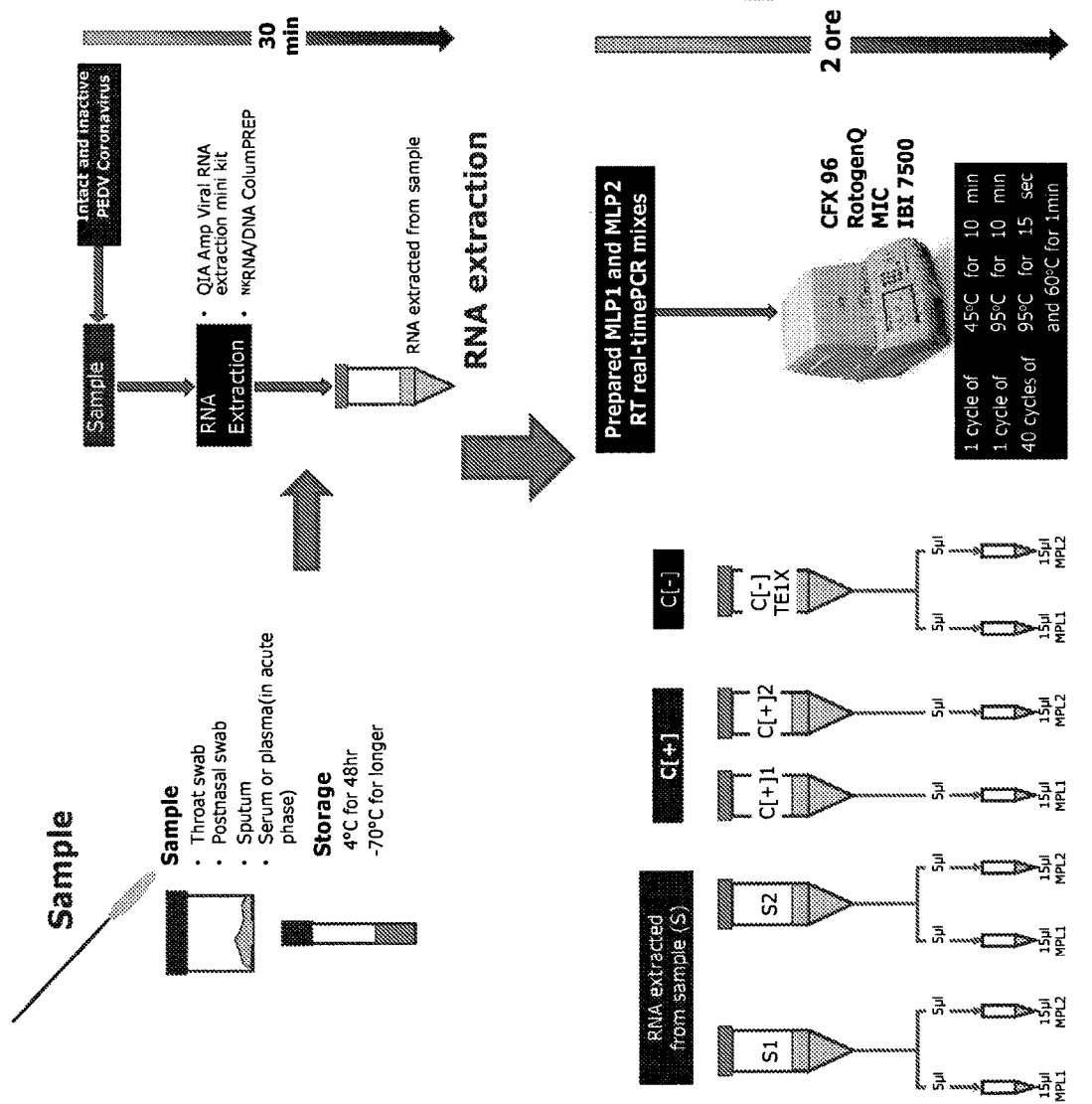
FIG. 19 schematically shows a diagnostic kit in accordance with the invention and its use.

Positive results rule out bacterial infection or co-infection with other coronaviruses. In addition, negative results unequivocally exclude SARS-CoV-2 infection. However, the results must always be combined with current clinical observations, with the patients' secondary co-morbidities, and with epidemiological information. In FIGS. 17 and 18 we reported four in-vivo cases respectively positive and negative for SARS-CoV-2. The patients were diagnosed in an authorized laboratory (Vietnam) connected with the University Pham Chau Trinh, Danang City, and the extracted RNA was re-checked by the kit for in-vivo quality control.

FIG. 17 shows two RNAs extracted from two patients who were positive for SARS-CoV-2 (COVID-19). The PEDV and E genes were amplified in each MPL2 of the patients (up left and right), MPL1 of patients 1 and 2 showed amplification of the specific targets of the N1, N2 and N3 genes of COVID-19. The in-vivo results determined a strong and highly sensitive positive outcome related to the presence of SARS-CoV-2.

FIG. 18 shows two RNAs extracted from 2 patients who were negative for SARS-CoV-2 (COVID-19). MPL1 detected only the presence of host epithelial cells, while MPL2 detected only the presence of PEDV. This indicated that these results were real and highly sensitive, not false or negatives.

SARS-CoV-2 is still in a phase of evolution and, as it was for the previous coronavirus pandemic infection, the COVID-19 tests currently available have shown some limitations. The main concerns are specifically related to false negative/positive outcomes, risks connected with the low sensitivity of the screening procedures, incongruous specimen collection measures, long sampling times and operator-dependent processing errors.

The WHO recommendation follows a similar procedure that was adopted during the SARS-CoV pandemic almost two decades ago. Sequential samples from suspected patients should be kept for future use, and health authorities should collect and store clinical history and contact data in order to generate a clear logarithm that shows the virus-specific traits and patterns and its way of diffusion. Patients' samples should be available for rRT-PCR analysis, virus culture, antigen detection and serological antibody assays. The WHO is warmly supporting local Governments in creating a capillary network of designated health task forces which include centres for prevention and treatment and laboratories for investigation and/or referral of specimens from possible COVID-19 patients.

The present invention is based, at least partly, on the recent encouraging outcomes achieved by the inventors during their COVID-19 research activities, with a view to produce a fast and reliable diagnostic tool based on rRT-PCR assay for detecting SARS-CoV-2 in humans.

The outcomes of the current rRT-PCR tests look promising, and the present test may offer a number of advantages:

(1) it is a one-step procedure, resulting in shorter diagnosis times. In fact, the entire procedure, including RNA extraction and rRT-PCR, requires less than 3 hours (operator-dependent time) and can be carried out in any laboratory equipped with Real Time PCR; (2) with this innovative rRT-PCR-based methodology it is possible to detect 4 Coronaviridae targets in a single procedure. The kit allows the user to detect all coronaviruses known as harmful pathogens for humans, including SARS-CoV, which causes SARS, SARS-CoV-2, which causes COVID-19, MERS-CoV, which causes MERS, and HCoV, which causes the flu; (3) a control procedure was set up in order to detect the presence of possible external and internal contamination and to validate the presence of negative outcomes, as well as to ensure a high level of sensitivity in the amplification phase through the DNA positive control; (4) a check-step was set up to avoid false negatives by using the porcine epidemic diarrhoea virus (PEDV-CoV) and Ribonuclease P (RNase P-RP) genes as internal controls.

The kit proposed herein detects and amplifies the viral nucleic acid isolated by using a standard extraction and purification kit. After purification, the nucleic acid is ready to be amplified in the Real-Time PCR (rRT-PCR) reaction. Each RNA target is then detected thanks to a specific green, yellow, orange or red fluorophore (or fluorochrome); fluorescence signals are measured by the Real-Time PCR instrument, which then provides the final result. The channels that need to be set up on the Plate Editor of the Real-Time PCR instrument are green (FAM), yellow (HEX), orange (TexasRED (R) and red (Cy5). In the first and second multiplex phases (MPL1-2), all target genes must be amplified.

The intent to include also different Coronaviridae members such as SARS-CoV, HCoV and MERS-CoV in this diagnostic procedure was mainly due to the atypical behaviour of COVID-19. In Italy we have been experiencing, since the end of 2019, a very unusual form of lung-flu disease, an infection that has shown many traits in common with the current COVID-19 disease.

The existing "pandemic" scenario requires solid and reliable diagnostic tests that will allow for the necessary decision making. A reliable, sensitive test like the one of the present invention will make it easier to organize and define any countermeasures that may be required in order to confront a pandemic outbreak and its consequences.

This test is faster than those currently in use due to at least four reasons: (i) the reagents for the One-Step rRT-PCR procedure that we chose to use are among the best as far as quality is concerned ("AgPath-ID™ One-Step RT-PCR" produced by Applied Biosystems-Thermo Fisher); (ii) The use of the enzymatic stabilizer makes it possible to pre-mix everything in the reaction, so that the user will not need to prepare the mix for the PCR analysis; (iii) The selected primers are targeted to the short fragment, so that there is no need to prolong the times of the extension reaction of the thermal cycle, and this will allow the user to reduce the PCR phase time to less than 1 hour; (iv) The amplification cycle for the RNA targets of the different coronaviruses occurs in a one-step amplification procedure via MPL1 and MPL2. In this single process, false negatives and false positives are also identified.

Furthermore, the test carried out by using the kit according to the present invention is fast and capable of ensuring a diagnostic certainty of 99.89%, compared with the one currently available on the market, which provides a diagnostic certainty of 70%. This is mainly due to the fact that test sensitivity is based on three factors: the first one is specimen collection (sensitivity is higher for sputum than for nasal swab, bronchial lavage is more sensitive than sputum), and this is not correlated with the test kit.

The second factor is related to kit quality, i.e. the quality of the RNA extraction kit and the quality of the reaction mix (Multiplex MPLT-2) for rRT-PCR. In our procedure, the PCR mix is prepared by using high-grade reagent and the best primers and probes, thus obtaining, as aforementioned, such a level of sensitivity that makes it possible to detect even just a few copies of the viral genome (exclusive regions) of the target pathogen in the reaction volume. The test carried out by using the invention is more sensitive that the traditional test, the sensitivity of which is approx. 70%.

This 70% value is reported in many studies and is mainly related to the quality of the sample and the quality of the test kit, as well as to the quality of the biological specimen and the operator-dependent variable.

The kit according to the invention includes two controls for verifying the quality while testing the sample: RNAse P (RP) for checking the sample quality, and PEDV for checking the coronavirus detection processing.

The result was deemed acceptable only when both quality tests had been passed. This to avoid false negatives and guarantee the high sensitivity of the test kit.

The rRT-PCR methodology confirms the full identification of the virus, making it possible to exclude the presence of contamination or false positives (exclusion of virus fragments in the host endothelial cells) or false negatives (exclusion of virus fragments that cannot be identified because in a non-identifiable number of copies).

This is the reason why the tests carried out with the kit of the invention can always be maintained at a high level of quality and sensitivity.

All of these features fall within the scope of the following claims.

The invention claimed is:

1. A diagnostic kit comprising a first quantitative reverse transcriptase PCR (rRT-PCR) master mix in a first container and a second rRT-PCR master mix in a second container, wherein the first rRT-PCR master mix in the first container comprises:
   a) three sets of primers and probes for detecting 3 genetic regions of the SARS-CoV-2 nucleocapsid, the three sets of primers and probes comprising primers and probes of SEQ ID NOs: 1-9,
   b) a set of primer and probes for detecting a genetic region of ribonuclease P (RP), the set of primers and probes comprising primers and probes of SEQ ID Nos: 10-12,
   c) a polymerase enzyme,
   d) an enzyme stabilizer, and
   e) a PCR buffer solution;
   wherein the second rRT-PCR master mix in the second container comprises:
   a) a set of primers and probes for detecting a genetic region for SARS-CoV upE, the set of primers and probes comprising primers and probes of SEQ ID NOs: 13-15,
   b) a set of primers and probes for detecting a genetic region for MERS-CoV HKU, the set of primers and probes comprising primers and probes of SEQ ID NOs: 22-24,
   c) a set of primers and probes for detecting a genetic region for PEDV-Virus N, the set of primers and probes comprising primers and probes of SEQ ID NOs: 16-18,
   d) a polymerase enzyme,
   e) an enzyme stabilizer, and
   f) a PCR buffer solution.

2. The diagnostic kit according to claim 1, further comprising a set of primers and probes having SEQ ID NOs: 19-21.

3. The diagnostic kit according to claim 1, comprising primers and probes of SEQ ID NOs: 1-24 as shown in the following table:

| first rRT-PCR master mix | Amount (pm) per 1 reaction | Stock (pm/μl) | Volume(μl) per 100 reactions |
|---|---|---|---|
| SEQ ID NO: 1 | 10 | 100 | 10 |
| SEQ ID NO: 2 | 10 | 100 | 10 |
| SEQ ID NO: 3 | 5 | 100 | 5 |
| SEQ ID NO: 4 | 10 | 100 | 10 |
| SEQ ID NO: 5 | 10 | 100 | 10 |
| SEQ ID NO: 6 | 5 | 100 | 5 |
| SEQ ID NO: 7 | 10 | 100 | 10 |
| SEQ ID NO: 8 | 10 | 100 | 10 |
| SEQ ID NO: 9 | 5 | 100 | 5 |
| SEQ ID NO: 10 | 2 | 100 | 2 |
| SEQ ID NO: 11 | 2 | 100 | 2 |
| SEQ ID NO: 12 | 5 | 100 | 5 |

| second rRT-PCR master mix | Amount (pm) per 1 reaction | Stock (pm/μl) | Volume(μl) per 100 reactions |
|---|---|---|---|
| SEQ ID NO: 13 | 10 | 100 | 10 |
| SEQ ID NO: 14 | 10 | 100 | 10 |
| SEQ ID NO: 15 | 5 | 100 | 5 |
| SEQ ID NO: 19 | 10 | 100 | 10 |
| SEQ ID NO: 20 | 10 | 100 | 10 |
| SEQ ID NO: 21 | 5 | 100 | 5 |
| SEQ ID NO: 16 | 10 | 100 | 10 |
| SEQ ID NO: 17 | 10 | 100 | 10 |
| SEQ ID NO: 18 | 5 | 100 | 5 |

-continued

| | | | |
|---|---|---|---|
| SEQ ID NO: 22 | 2 | 100 | 2 |
| SEQ ID NO: 23 | 2 | 100 | 2 |
| SEQ ID NO: 24 | 5 | 100 | 5. |

4. The diagnostic kit according to claim 1, wherein the polymerase enzyme is a Taq polymerase.

5. The diagnostic kit according to claim 1, further comprising a synthetic fragment of Porcine Epidemic Diarrhoea Virus (PEDV) DNA.

6. A method of detecting a coronavirus in a sample from a subject, the method comprising obtaining the sample from the subject, testing the sample using the diagnostic kit of claim 1, and detecting that the sample contains the coronavirus.

7. The method of claim 6, wherein the coronavirus is Severe Acute Respiratory Syndrome Coronavirus 2 (SARS-CoV-2), SARS-CoV, Middle East Respiratory Syndrome coronavirus (MERS-CoV), or Human Coronavirus (HCoV).

8. The diagnostic kit of claim 1, further comprising a spin column, a proteinase K, a binding buffer solution, a first washing buffer solution, a second washing buffer solution, a third washing buffer solution, and an elution buffer.

\* \* \* \* \*

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: N1-F2019-nCoV

<400> SEQUENCE: 1
gaccccaaaa tcagcgaaat                                          20

```
<210> SEQ ID NO 2
<211> LENGTH: 24
<212> TYPE: DNA
<213> ORGANISM: Artificial Sequence
<220> FEATURE:
<223> OTHER INFORMATION: N1-R2019-nCoV

<400> SEQUENCE: 2
tctggttact gccagttgaa tctg                                              24

<210> SEQ ID NO 3
<211> LENGTH: 24
<212> TYPE: DNA
<213> ORGANISM: Artificial Sequence
<220> FEATURE:
<223> OTHER INFORMATION: N1Probe

<400> SEQUENCE: 3
accccgcatt acgtttggtg gacc                                              24

<210> SEQ ID NO 4
<211> LENGTH: 20
<212> TYPE: DNA
<213> ORGANISM: Artificial Sequence
<220> FEATURE:
<223> OTHER INFORMATION: N2-F2019-nCoV

<400> SEQUENCE: 4
ttacaaacat tggccgcaaa                                                   20

<210> SEQ ID NO 5
<211> LENGTH: 18
<212> TYPE: DNA
<213> ORGANISM: Artificial Sequence
<220> FEATURE:
<223> OTHER INFORMATION: N2-R2019-nCoV

<400> SEQUENCE: 5
gcgcgacatt ccgaagaa                                                     18

<210> SEQ ID NO 6
<211> LENGTH: 23
<212> TYPE: DNA
<213> ORGANISM: Artificial Sequence
<220> FEATURE:
<223> OTHER INFORMATION: N2Probe

<400> SEQUENCE: 6
acaatttgcc cccagcgctt cag                                               23

<210> SEQ ID NO 7
<211> LENGTH: 22
<212> TYPE: DNA
<213> ORGANISM: Artificial Sequence
<220> FEATURE:
<223> OTHER INFORMATION: N3-F2019-nCoV

<400> SEQUENCE: 7
gggagccttg aatacaccaa aa                                                22

<210> SEQ ID NO 8
<211> LENGTH: 21
<212> TYPE: DNA
<213> ORGANISM: Artificial Sequence
<220> FEATURE:
<223> OTHER INFORMATION: N3-R2019-nCoV
```

-continued

<400> SEQUENCE: 8
tgtagcacga ttgcagcatt g                                      21

<210> SEQ ID NO 9
<211> LENGTH: 24
<212> TYPE: DNA
<213> ORGANISM: Artificial Sequence
<220> FEATURE:
<223> OTHER INFORMATION: N3Probe

<400> SEQUENCE: 9
aycacattgg cacccgcaat cctg                                   24

<210> SEQ ID NO 10
<211> LENGTH: 19
<212> TYPE: DNA
<213> ORGANISM: Artificial Sequence
<220> FEATURE:
<223> OTHER INFORMATION: RP-F

<400> SEQUENCE: 10
agatttggac ctgcgagcg                                         19

<210> SEQ ID NO 11
<211> LENGTH: 20
<212> TYPE: DNA
<213> ORGANISM: Artificial Sequence
<220> FEATURE:
<223> OTHER INFORMATION: RP-R

<400> SEQUENCE: 11
gagcggctgt ctccacaagt                                        20

<210> SEQ ID NO 12
<211> LENGTH: 23
<212> TYPE: DNA
<213> ORGANISM: Artificial Sequence
<220> FEATURE:
<223> OTHER INFORMATION: RP-P

<400> SEQUENCE: 12
ttctgacctg aaggctctgc gcg                                    23

<210> SEQ ID NO 13
<211> LENGTH: 26
<212> TYPE: DNA
<213> ORGANISM: Artificial Sequence
<220> FEATURE:
<223> OTHER INFORMATION: E_Sarbeco_F1

<400> SEQUENCE: 13
acaggtacgt taatagttaa tagcgt                                 26

<210> SEQ ID NO 14
<211> LENGTH: 22
<212> TYPE: DNA
<213> ORGANISM: Artificial Sequence
<220> FEATURE:
<223> OTHER INFORMATION: E_Sarbeco_R2

<400> SEQUENCE: 14
atattgcagc agtacgcaca ca                                     22

<210> SEQ ID NO 15
<211> LENGTH: 26

```
<212> TYPE: DNA
<213> ORGANISM: Artificial Sequence
<220> FEATURE:
<223> OTHER INFORMATION: E_Sarbeco_P1

<400> SEQUENCE: 15
acactagcca tccttactgc gcttcg                                        26

<210> SEQ ID NO 16
<211> LENGTH: 21
<212> TYPE: DNA
<213> ORGANISM: Artificial Sequence
<220> FEATURE:
<223> OTHER INFORMATION: PEDVNFedit3

<400> SEQUENCE: 16
gcgcaaagac tgaacccact a                                             21

<210> SEQ ID NO 17
<211> LENGTH: 24
<212> TYPE: DNA
<213> ORGANISM: Artificial Sequence
<220> FEATURE:
<223> OTHER INFORMATION: PEDVNR

<400> SEQUENCE: 17
ttgcctctgt tgttacttgg agat                                          24

<210> SEQ ID NO 18
<211> LENGTH: 24
<212> TYPE: DNA
<213> ORGANISM: Artificial Sequence
<220> FEATURE:
<223> OTHER INFORMATION: PEDV-HEX(RV)

<400> SEQUENCE: 18
tgttgccatt gccacgactc ctgc                                          24

<210> SEQ ID NO 19
<211> LENGTH: 18
<212> TYPE: DNA
<213> ORGANISM: Artificial Sequence
<220> FEATURE:
<223> OTHER INFORMATION: upE_TqF

<400> SEQUENCE: 19
gcaacgcgcg attcagtt                                                 18

<210> SEQ ID NO 20
<211> LENGTH: 20
<212> TYPE: DNA
<213> ORGANISM: Artificial Sequence
<220> FEATURE:
<223> OTHER INFORMATION: upE_tqR

<400> SEQUENCE: 20
gcctctacac gggacccata                                               20

<210> SEQ ID NO 21
<211> LENGTH: 26
<212> TYPE: DNA
<213> ORGANISM: Artificial Sequence
<220> FEATURE:
<223> OTHER INFORMATION: upE_TqPR (TexasRED)

<400> SEQUENCE: 21
```

-continued

```
ctcttcacat aatcgccccg agctcg                                      26

<210> SEQ ID NO 22
<211> LENGTH: 19
<212> TYPE: DNA
<213> ORGANISM: Artificial Sequence
<220> FEATURE:
<223> OTHER INFORMATION: HCoV-HKU-1-F

<400> SEQUENCE: 22
ccttgcgaat gaatgtgct                                              19

<210> SEQ ID NO 23
<211> LENGTH: 24
<212> TYPE: DNA
<213> ORGANISM: Artificial Sequence
<220> FEATURE:
<223> OTHER INFORMATION: HCoV-HKU-1-R

<400> SEQUENCE: 23
ttgcatcacc actgctagta ccac                                        24

<210> SEQ ID NO 24
<211> LENGTH: 30
<212> TYPE: DNA
<213> ORGANISM: Artificial Sequence
<220> FEATURE:
<223> OTHER INFORMATION: HCoV-HKU-1-PR

<400> SEQUENCE: 24
tgtgtggcgg ttgctattat gttaagcctg                                  30
```